United States Patent [19]

Bell et al.

[11] Patent Number: 5,336,615
[45] Date of Patent: Aug. 9, 1994

[54] GENETICALLY ENGINEERED ENDOTHELIAL CELLS EXHIBITING ENHANCED MIGRATION AND PLASMINOGEN ACTIVATOR ACTIVITY

[75] Inventors: Leonard Bell, Woodbridge; Joseph A. Madri, North Branford; Stephen L. Warren, Orange, all of Conn.; Daniel J. Luthringer, Beverly Hills, Calif.

[73] Assignee: Yale University, New Haven, Conn.

[21] Appl. No.: 820,011

[22] Filed: Jan. 6, 1992

[51] Int. Cl.$^5$ .................... C12N 5/10; C12N 5/06; C12N 15/85; A61F 2/06
[52] U.S. Cl. ........................... 435/240.2; 424/423; 424/93.21; 600/36; 623/1; 435/32.01; 435/172.3; 435/240.243; 935/70; 935/71
[58] Field of Search .............. 483/240.2, 172.3, 320.1, 483/91; 536/27, 23.1, 23.5, 23.2; 435/240.21, 240.243; 935/59, 60, 62, 70, 71; 600/36; 623/1, 11, 66; 424/938, 934, 423

[56] References Cited

PUBLICATIONS

Perlmutter et al., 1988 Biochim. Biophys. Acta 948, 245–262.
Anderson, S. K., C. P. Gibbs, A. Tanaka, H. Kung, and D. Fujita. 1985. "Human Cellular src Gene; Nucleotide Sequence and Derived Amino Acid Sequence of the Region Coding for the Carboxy-Terminal Two-Thirds of pp. 60$^{c-src}$", *Molecular and Cellular Biology.* 5:1122–1129.
Azarnia, R., S. Reddy, T. E. Kmiecik, D. Shalloway, and W. R. Loewenstein, 1988. "The Cellular *src* Gene Product Regulates Junctional Cell-to-Cell Communication", *Science.* 23:398–401.
Bell, L. and J. A. Madri, 1989, "Effect of platelet factors on migration of cultured bovine aortic endothelial and smooth muscle cells", *Circ. Res.* 65:1057–1065.
Bell, L. and J. A. Madri. 1990. "Influence of the angiotensin system on endothelial and smooth muscle cell migration", *Am. J. Pathol.* 137:7–12.
Bell, S. M., R. W. Brackenbury, N. D. Leslie and J. L. Degen. 1990. "Plasminogen activator gene expression is induced by the src oncogene product and tumor promoters", *J. Biol. Chem.* 265:1333–1338.
Blake, M. S., K. H. Johnston, G. J. Russell–Jones and E. C. Gotschlich. 1984. "A rapid, sensitive method for detection of alkaline phosphatase–conjugated anti–antibody of alkaline phosphatase–conjugated anti–antibody on Western blots", *Anal. Biochem.* 136:175–179.
Caldwell, R. R. B., B. C. Seegal, and K. C. Hsu. 1976. "Antiotensin–converting enzyme: vascular endothelial localization", *Science (Wash. DC).* 191:1050–1051.
Cone, R. D. and R. C. Mulligan. 1984. "High–efficiency gene transfer into mammalian cells: generation of helper-free recombinant retrovirus with broad mammalian host range", *Proc. Natl. Acad. Sci.* 81:6349–6353.
Culliton B. J. 1989. "Designing Cells to Deliver Drugs", *Science.* 246:746–751.
Dichek, D. A., R. F. Neville, J. A. Zwiebel, S. Freeman, M. B. Leon, and W. F. Anderson. 1989.
(List continued on next page.)

Primary Examiner—Christopher S. F. Low
Attorney, Agent, or Firm—Maurice M. Klee

[57] ABSTRACT

Genetically engineered endothelial cells which exhibit enhanced cell migration and enhanced urokinase-type plasminogen activator (u-PA) activity are provided. The cells are modified by incorporation of the coding sequence for the c-src gene so that the cells express elevated levels of the tyrosine kinase protein, pp60$^{c-src}$. The C-src gene is a naturally occurring gene which appears to be present in all animal species and is highly conserved. Because of their enhanced migration rates, the modified cells can be used to efficiently seed denuded segments of vessels or natural or synthetic grafts prior to implantation. Because of their enhanced u-PA activity, the cells can reduce the probability of thrombus formation at sites of vessel damage, such as that produced during such surgical procedures as coronary angioplasty and vessel reconstruction with grafts, stents, or the like.

19 Claims, 6 Drawing Sheets

PUBLICATIONS

"Seeding of Intravascular Stents with Genetically Engineered Endothelial Cells", *Circulation.* 80:1347–1353.

DiSalvo, J. D. Gifford, and A. Kokkinakis. 1988. "pp. 60$^{c-src}$ kinase activity in bovine coronary extracts is stimulated by ATP", *Biochem. Biophys. Res. Commun.* 153:388–394.

Dorai, T., and L. H. Wang. 1990. "An alternative non–tyrosine protein kinase product of the c–src gene in chicken skeletal muscle", *Mol. Cell. Biol.* 10:4068–4079.

Fasol, R., P. Zilla, M. Deutsch, M. Grimm, T. Fischlein, and G. Laugfer. 1989. "Human endothelial cell seeding: Evaluation of its effectiveness by platelet parameters after one year", *Journal of Vascular Surgery.* 9:432–436.

Fishman, J. A., G. B. Ryan, M. J. Karnovsky. 1975. "Endothelial regeneration in the rat carotid artery and the significance of endothelial denudation in the pathogenesis of myointimal thickening", *Laboratory Investigation.* 32:339–351.

Granelli–Piperino, A. and E. Reich. 1978. "A study of proteases and protease–inhibitor complexes in biological fluids", *J. Exp. Med.* 148:223–234.

Haudenschild, C. C. and S. M. Schwartz. 1979. "Endothelial regeneration: II. Restitution of endothelial continuity", *Laboratory Investigation.* 41:407–418.

Hunter, T. 1987. "A Tail of Two *src's*: Mutatis Mutandis", *Cell.* 49:1–4.

Johnson, A. R., and E. G. Erdos. 1977. "Metabolism of vasoactive peptides by human endothelial cells in culture: angiotension I converting enzyme (kininase II) and angiotensinase", *J. Clin. Invest.* 59:684–695.

Jove, R., S. Kornbluth and H. Hanafusa. 1987. "Enzymatically inactive p60c–src mutant with altered ATP–binding site is fully phosphorylated in its carboxy–terminal regulatory region", *Cell.* 50:937–43.

Knecht, D. A. and R. L. Dimond. 1984. "Visualization of antigenic proteins on Wester blots", *Anal. Biochem.* 136:180–184.

Koch, C. A., D. Anderson, M. F. Moran, C. Ellis, and T. Pawson. 1991 "SH2 and SH3 domains: elements that control interactions of cytoplasmic signaling proteins", *Science* 252:668–674).

Levy, J. B., H. Iba, and H. Hanafusa. 1986. "Activation of the transforming potential of pp. 60$^{c-src}$ by a single amino acid change", *Proc. Natl. Acad. Sci. USA* 83:4228–4232.

Lilly, L. S., R. E. Pratt, R. W. Alexander, D. M. Larson, K. E. Ellison, M. A. Gimbrone, and V. J. Dzau. 1985. "Renin expression by vascular endothelial cells in culture", *Circ. Res.* 57:312–318.

Loewenstein, W. R., and R. Azarnia. 1988. "Regulation of Intercellular Communication and Growth by the Cellular *src* Gene", *Annals New York Academy of Sciences,* 551:337–346.

Madri, J. A., M. A. Reidy, O. Kocher, and L. Bell. 1989. "Endothelial cell behavior following denudation injury is modulated by TGF–B1 and fibronectin", *Laboratory Investigation.* 60:755–765.

Mahmoudi, M. and V. K. Lin. 1989. "Comparison of Two different hybridization systems in Northern transfer analysis", *Biotech* 7:331–333.

Maniatis, T., E. F. Fritsch and J. Sambrook. 1982. *Molecular cloning: a laboratory manual.* Cold Spring Harbor Laboratory, Cold Spring Harbor, NY. 196.

Mann, R., R. C. Mulligan, and D. Baltimore. 1983. "Construction of a Retrovirus Packaging Mutant and Its Use to Produce Helper–Free Defective Retrovirus", *Cell.* 33: 153–159.

Nabel, E. G., G. Plautz, F. M. Boyce, J. C. Stanley, and G. J. Nabel. 1989. "Recombinant Gene Expression *in Vivo* Within Endothelial Cells of the Arterial Wall", *Science.* 244:1342–1343.

Nabel, E. G., G. Plautz, and G. J. Nabel. 1990. "Site-Specific Gene Expression *in Vivo* by Direct Gene Transfer into the Arterial Wall", *Science,* 249:1285–1288.

Ortenwall, P., H. Wadevik, J. Kutti, and B. Risberg. 1990. "Endothelial cell seeding reduces thrombogenicity of Dacron grafts in humans", *Journal of Vascular Surgery.* 11:403–410.

Patel, J. M., F. R. Yarid, E. R. Block, and M. K. Raizda. 1989. "Angiotensin receptors in pulmonary arterial and aortic endothelial cells", *Am. J. Physiol.* 256:C987–C993.

Reidy, M. A. and S. M. Schwartz. 1981. "Endothelial regeneration: III. Time course of intimal changes after small defined injury to rat aortic endothelium", *Laboratory Investigation.* 44:301–308.

Ryan, U. S., J. W. Ryan, C. Whitaker, and A. Chiu. 1976. "Localization of angiotensin converting enzyme (kininase II). II. Immunocytochemistry and immunofluorescence ", *Tissue Cell.* 8:125–145.

(List continued on next page.)

PUBLICATIONS

Saksela, O., and D. B. Rifkin. 1990. "Release of basic fibroblast growth factor-heparan sulfate complexes from endothelial cells by plasminogen activator-mediated proteolytic activity", *J. Cell Biol.* 110:767–775.

Schwartz, S. M., C. C. Haudenschild, and E. M. Eddy. 1978. "Endothelial regeneration: I. Quantitative analysis of initial stages of endothelial regeneration in rat aortic intima", *Laboratory investigation.* 38:568–580.

Shalloway, D., P. M. Coussens, and P. Yaciuk. 1984. "Overexpression of the C-*src* Protein Does Not Induce Transformation of NIH 3T3 Cells", *Proc. Natl. Acad. Sci. USA.* 81:7071–7075.

Smith, P. K., R. I. Krohn, G. T. Hermansion, A. K. Mallia, F. H. Gartner, M. D. Provenzano, E. K. Fujimoto, N. M. Goeke, B. J. Olson and D. C. Klenk, 1985. "Measurement of protein using bicinchonic acid", *Anal. Biochem.* 150:76–85.

Soriano, P., C. Montgomery, R. Geske, and A. Bradley. 1991. "Targeted Disruption of the c-*src* Proto-Oncogene Leads to Osteopetrosis in Mice", *Cell.* 64:693–702.

Spector, D., H. E. Varmus, and J. M. Bishop. 1978a. "Nucleotide sequences related to the transforming gene of avian sarcoma virus are present in DNA of uninfected vertebrates", *Proc. Nat. Acad. Sci. USA.* 75:4102–4106.

Stehelin, D., H. E. Varmus, J. M. Bishop, and P. K. Vogt. 1976. "DNA related to the transforming gene(s) of avian sarcoma viruses is present in normal avian DNA", *Nature.* 260:170–173.

Takeya, T. and H. Hanafusa. 1983. "Structure and Sequence of the Cellular Gene Homologous to the RSV *src* Gene and the Mechanism for Generating the Transforming Virus", *Cell.* 32:881–890.

Tanaka, A., C. P. Gibbs, R. R. Arthur, S. K. Anderson, H. Kung, and D. Fujita. 1987. "DNA Sequence Encoding the Amino-Terminal Region of the Human C-*src* Protein: implications of Sequence Divergence among src-Type Kinase Oncogenes", *Molecular and Cellular Biology.* 7:1978–1983.

Varmus, H. E. 1982. "Form and Function of Retroviral Proviruses", *Science.* 216:812–820.

Warren, S. L., L. M. Handel and W. J. Nelson. 1988. "Elevated expression of $pp60^{c-src}$ alters a selective morphogenetic property of epithelial cells in vitro without a mitogenic effect", *Mol. Cell. Biol.* 8:632–646.

Wilson, J. M., L. K. Birinyi, R. N. Salomon, P. Libby, A. D. Callow, and R. C. Mulligan. 1989. "Implantation of Vascular Grafts Lined with Genetically Modified Endothelial Cells", *Science.* 244:1344–1346.

Zilla, P., R. Fasol, M. Deutsch, T. Fischlein, E. Minar, A. Hammerle, O. Krapicka, and M. Kadietz. 1987. "Endothelial cell seeding of polytetrafluoroethylene vascular grafts in humans: A preliminary report", *Journal of Vascular Surgery.* 6:535–541.

Zwiebel, J. A., S. M. Freeman, P. W. Kantoff, K. Cornetta, U. S. Ryan, and W. F. Anderson. 1989. "Highthelial Cells Transduced by Retroviral Vectors", *Science.* 243:220–222.

-Level Recombinant Gene Expression in Rabbit Endo-

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 1602 base pairs
        ( B ) TYPE: Nucleic Acid
        ( C ) STRANDEDNESS: Double
        ( D ) TOPOLOGY: Linear ( i i ) MOLECULE TYPE: cDNA to mRNA ( i i i ) HYPOTHETICAL: No ( i v ) ANTI-SENSE: No ( v i ) ORIGINAL SOURCE:
        ( A ) ORGANISM: Gallus, gallus ( x ) PUBLICATION INFORMATION:
        ( A ) AUTHORS: Takeya, Tatsuo
                  Hanafusa, Hidesaburo
        ( B ) TITLE: Structure and Sequence of the
                Cellular Gene Homologous to the RSV src
                Gene and the Mechanism for Generating the
                Transforming Virus
        ( C ) JOURNAL: Cell
        ( D ) VOLUME: 32
        ( F ) PAGES: 881-890
        ( G ) DATE: March, 1983

( x i ) SEQUENCE DESCRIPTION: SEQ ID NO:1:

```
ATG  GGG  AGC  AGC  AAG  AGC  AAG  CCC  AAG  GAC  CCC  AGC  CAG  CGC  CGG  CGC      48
Met  Gly  Ser  Ser  Lys  Ser  Lys  Pro  Lys  Asp  Pro  Ser  Gln  Arg  Arg  Arg
                    5                   10                      15

AGC  CTG  GAG  CCA  CCC  GAC  AGC  ACC  CAC  CAC  GGG  GGA  TTC  CCA  GCC  TCG      96
Ser  Leu  Glu  Pro  Pro  Asp  Ser  Thr  His  His  Gly  Gly  Phe  Pro  Ala  Ser
                    20                  25                      30

CAG  ACC  CCC  AAC  AAG  ACA  GCA  GCC  CCC  GAC  ACG  CAC  CGC  ACC  CCC  AGC     144
Gln  Thr  Pro  Asn  Lys  Thr  Ala  Ala  Pro  Asp  Thr  His  Arg  Thr  Pro  Ser
               35                   40                      45

CGC  TCC  TTT  GGG  ACC  GTG  GCC  ACC  GAG  CCC  AAG  CTC  TTC  GGG  GGC  TTC     192
Arg  Ser  Phe  Gly  Thr  Val  Ala  Thr  Glu  Pro  Lys  Leu  Phe  Gly  Gly  Phe
               50                   55                      60

AAC  ACT  TCT  GAC  ACC  GTT  ACG  TCG  CCG  CAG  CGT  GCC  GGG  GCA  CTG  GCT     240
Asn  Thr  Ser  Asp  Thr  Val  Thr  Ser  Pro  Gln  Arg  Ala  Gly  Ala  Leu  Ala
65                       70                   75                          80

GGC  GGC  GTC  ACC  ACT  TTC  GTG  GCT  CTC  TAC  GAC  TAC  GAG  TCC  CGG  ACT     288
Gly  Gly  Val  Thr  Thr  Phe  Val  Ala  Leu  Tyr  Asp  Tyr  Glu  Ser  Arg  Thr
                    85                   90                      95

GAA  ACG  GAC  TTG  TCC  TTC  AAG  AAA  GGA  GAA  CGC  CTG  CAG  ATT  GTC  AAC     336
Glu  Thr  Asp  Leu  Ser  Phe  Lys  Lys  Gly  Glu  Arg  Leu  Gln  Ile  Val  Asn
                    100                  105                     110
```

| | | | | | | | | | | | | | | | | |
|---|---|---|---|---|---|---|---|---|---|---|---|---|---|---|---|---|
| AAC | ACG | GAA | GGT | GAC | TGG | TGG | CTG | GCT | CAT | TCC | CTC | ACT | ACA | GGA | CAG | 384 |
| Asn | Thr | Glu | Gly | Asp | Trp | Trp | Leu | Ala | His | Ser | Leu | Thr | Thr | Gly | Gln | |
| | | 115 | | | 120 | | | | | | | 125 | | | | |
| ACG | GGC | TAC | ATC | CCC | AGT | AAC | TAT | GTC | GCG | CCC | TCA | GAC | TCC | ATC | CAG | 432 |
| Thr | Gly | Tyr | Ile | Pro | Ser | Asn | Tyr | Val | Ala | Pro | Ser | Asp | Ser | Ile | Gln | |
| | 130 | | | | 135 | | | | | 140 | | | | | | |
| GCT | GAA | GAG | TGG | TAC | TTT | GGG | AAG | ATC | ACT | CGT | CGG | GAG | TCC | GAG | CGG | 480 |
| Ala | Glu | Glu | Trp | Tyr | Phe | Gly | Lys | Ile | Thr | Arg | Arg | Glu | Ser | Glu | Arg | |
| 145 | | | | | 150 | | | | | 155 | | | | | 160 | |
| CTG | CTG | CTC | AAC | CCC | GAA | AAC | CCC | CGG | GGA | ACC | TTC | TTG | GTC | CGG | GAG | 528 |
| Leu | Leu | Leu | Asn | Pro | Glu | Asn | Pro | Arg | Gly | Thr | Phe | Leu | Val | Arg | Glu | |
| | | | | 165 | | | | | 170 | | | | | 175 | | |
| AGC | GAG | ACG | ACA | AAA | GGT | GCC | TAT | TGC | CTC | TCC | GTT | TCT | GAC | TTT | GAC | 576 |
| Ser | Glu | Thr | Thr | Lys | Gly | Ala | Tyr | Cys | Leu | Ser | Val | Ser | Asp | Phe | Asp | |
| | | | 180 | | | | | 185 | | | | | 190 | | | |
| AAC | GCC | AAG | GGG | CTC | AAT | GTG | AAG | CAC | TAC | AAG | ATC | CGC | AAG | CTG | GAC | 624 |
| Asn | Ala | Lys | Gly | Leu | Asn | Val | Lys | His | Tyr | Lys | Ile | Arg | Lys | Leu | Asp | |
| | | 195 | | | | 200 | | | | | 205 | | | | | |
| AGC | GGC | GGC | TTC | TAC | ATC | ACC | TCA | CGC | ACA | CAG | TTC | AGC | AGC | CTG | CAG | 672 |
| Ser | Gly | Gly | Phe | Tyr | Ile | Thr | Ser | Arg | Thr | Gln | Phe | Ser | Ser | Leu | Gln | |
| | 210 | | | | | 215 | | | | | 220 | | | | | |
| CAG | CTG | GTG | GCC | TAC | TAC | TCC | AAA | CAT | GCT | GAT | GGC | TTG | TGC | CAC | CGC | 720 |
| Gln | Leu | Val | Ala | Tyr | Tyr | Ser | Lys | His | Ala | Asp | Gly | Leu | Cys | His | Arg | |
| 225 | | | | 230 | | | | | 235 | | | | | | 240 | |
| CTG | ACC | AAC | GTC | TGC | CCC | ACG | TCC | AAG | CCC | CAG | ACC | CAG | GGA | CTC | GCC | 768 |
| Leu | Thr | Asn | Val | Cys | Pro | Thr | Ser | Lys | Pro | Gln | Thr | Gln | Gly | Leu | Ala | |
| | | | | 245 | | | | | 250 | | | | | 255 | | |
| AAG | GAC | GCG | TGG | GAA | ATC | CCC | CGG | GAG | TCG | CTG | CGG | CTG | GAG | GTG | AAG | 816 |
| Lys | Asp | Ala | Trp | Glu | Ile | Pro | Arg | Glu | Ser | Leu | Arg | Leu | Glu | Val | Lys | |
| | | | 260 | | | | | 265 | | | | | 270 | | | |
| CTG | GGG | CAG | GGC | TGC | TTT | GGA | GAG | GTC | TGG | ATG | GGG | ACC | TGG | AAC | GGC | 864 |
| Leu | Gly | Gln | Gly | Cys | Phe | Gly | Glu | Val | Trp | Met | Gly | Thr | Trp | Asn | Gly | |
| | | 275 | | | | | 280 | | | | | 285 | | | | |
| ACC | ACC | AGA | GTG | GCC | ATA | AAG | ACT | CTG | AAG | CCC | GGC | AAC | ATG | TCC | CCG | 912 |
| Thr | Thr | Arg | Val | Ala | Ile | Lys | Thr | Leu | Lys | Pro | Gly | Asn | Met | Ser | Pro | |
| | 290 | | | | | 295 | | | | | 300 | | | | | |
| GAG | GCC | TTC | CTG | CAG | GAA | GCC | CAA | GTG | ATG | AAG | AAG | CTC | CGG | CAT | GAG | 960 |
| Glu | Ala | Phe | Leu | Gln | Glu | Ala | Gln | Val | Met | Lys | Lys | Leu | Arg | His | Glu | |
| 305 | | | | | 310 | | | | | 315 | | | | | 320 | |
| AAG | CTG | GTT | CAG | CTG | TAC | GCA | GTG | GTG | TCG | GAA | GAG | CCC | ATC | TAC | ATC | 1008 |
| Lys | Leu | Val | Gln | Leu | Tyr | Ala | Val | Val | Ser | Glu | Glu | Pro | Ile | Tyr | Ile | |
| | | | | 325 | | | | | 330 | | | | | 335 | | |
| GTC | ACT | GAG | TAC | ATG | AGC | AAG | GGG | AGC | CTC | CTG | GAT | TTC | CTG | AAG | GGA | 1056 |
| Val | Thr | Glu | Tyr | Met | Ser | Lys | Gly | Ser | Leu | Leu | Asp | Phe | Leu | Lys | Gly | |
| | | | 340 | | | | | 345 | | | | | 350 | | | |
| GAG | ATG | GGC | AAG | TAC | CTG | CGG | CTG | CCA | CAG | CTC | GTC | GAT | ATG | GCT | GCT | 1104 |
| Glu | Met | Gly | Lys | Tyr | Leu | Arg | Leu | Pro | Gln | Leu | Val | Asp | Met | Ala | Ala | |
| | | 355 | | | | | 360 | | | | | 365 | | | | |
| CAG | ATT | GCA | TCC | GGC | ATG | GCC | TAT | GTG | GAG | AGG | ATG | AAC | TAC | GTG | CAC | 1152 |
| Gln | Ile | Ala | Ser | Gly | Met | Ala | Tyr | Val | Glu | Arg | Met | Asn | Tyr | Val | His | |
| | 370 | | | | | 375 | | | | | 380 | | | | | |
| CGA | GAC | CTG | CGG | GCG | GCC | AAC | ATC | CTG | GTG | GGG | GAG | AAC | CTG | GTG | TGC | 1200 |
| Arg | Asp | Leu | Arg | Ala | Ala | Asn | Ile | Leu | Val | Gly | Glu | Asn | Leu | Val | Cys | |
| 385 | | | | | 390 | | | | | 395 | | | | | 400 | |
| AAG | GTG | GCT | GAC | TTT | GGG | CTG | GCA | CGC | CTC | ATC | GAG | GAC | AAC | GAG | TAC | 1248 |
| Lys | Val | Ala | Asp | Phe | Gly | Leu | Ala | Arg | Leu | Ile | Glu | Asp | Asn | Glu | Tyr | |
| | | | | 405 | | | | | 410 | | | | | 415 | | |
| ACA | GCA | CGG | CAA | GGT | GCC | AAG | TTC | CCC | ATC | AAG | TGG | ACA | GCC | CCC | GAG | 1296 |
| Thr | Ala | Arg | Gln | Gly | Ala | Lys | Phe | Pro | Ile | Lys | Trp | Thr | Ala | Pro | Glu | |
| | | | 420 | | | | | 425 | | | | | 430 | | | |
| GCA | GCC | CTC | TAT | GGC | CGG | TTC | ACC | ATC | AAG | TCG | GAT | GTC | TGG | TCC | TTC | 1344 |
| Ala | Ala | Leu | Tyr | Gly | Arg | Phe | Thr | Ile | Lys | Ser | Asp | Val | Trp | Ser | Phe | |

|                                   |                             |                                   |      |
|---|---|---|---|
| 435 | 440 | 445 | |
| GGC ATC CTG CTG ACT GAG CTG ACC ACC AAG GGC CGG GTG CCA TAC CCA<br>Gly Ile Leu Leu Thr Glu Leu Thr Thr Lys Gly Arg Val Pro Tyr Pro<br>450 455 460 | | | 1392 |
| GGG ATG GTC AAC AGG GAG GTG CTG GAC CAG GTG GAG AGG GGC TAC CGC<br>Gly Met Val Asn Arg Glu Val Leu Asp Gln Val Glu Arg Gly Tyr Arg<br>465 470 475 480 | | | 1440 |
| ATG CCC TGC CCG CCC GAG TGC CCC GAG TCG CTG CAT GAC CTC ATG TGC<br>Met Pro Cys Pro Pro Glu Cys Pro Glu Ser Leu His Asp Leu Met Cys<br>485 490 495 | | | 1488 |
| CAG TGC TGG CGG AGG GAC CCT GAG GAG CGG CCC ACT TTT GAG TAC CTG<br>Gln Cys Trp Arg Arg Asp Pro Glu Glu Arg Pro Thr Phe Glu Tyr Leu<br>500 505 510 | | | 1536 |
| CAG GCC TTC CTG GAG GAC TAC TTC ACC TCG ACA GAG CCC CAG TAC CAG<br>Gln Ala Phe Leu Glu Asp Tyr Phe Thr Ser Thr Glu Pro Gln Tyr Gln<br>515 520 525 | | | 1584 |
| CCT GGA GAG AAC CTA TAG<br>Pro Gly Glu Asn Leu<br>530 | | | 1602 |

( 2 ) INFORMATION FOR SEQ ID NO:2:

( i ) SEQUENCE CHARACTERISTICS:
        ( A ) LENGTH: 533 amino acids
        ( B ) TYPE: Amino Acid
        ( D ) TOPOLOGY: Linear ( i i ) MOLECULE TYPE: Protein ( i i i ) HYPOTHETICAL: No ( v ) FRAGMENT TYPE: Complete Sequence ( v i ) ORIGINAL SOURCE:
        ( A ) ORGANISM: Gallus, gallus ( x ) PUBLICATION INFORMATION:
        ( A ) AUTHORS: Takeya, Tatsuo
                      Hanafusa, Hidesaburo
        ( B ) TITLE: Structure and Sequence of the
                  Cellular Gene Homologous to the RSV src
                  Gene and the Mechanism for Generating the
                  Transforming Virus
        ( C ) JOURNAL: Cell
        ( D ) VOLUME: 32
        ( F ) PAGES: 881-890
        ( G ) DATE: March, 1983

( x i ) SEQUENCE DESCRIPTION: SEQ ID NO:2:

| | | | | | | | | | | | | | | | |
|---|---|---|---|---|---|---|---|---|---|---|---|---|---|---|---|
| Met | Gly | Ser | Ser | Lys<br>5 | Ser | Lys | Pro | Lys | Asp<br>10 | Pro | Ser | Gln | Arg | Arg<br>15 | Arg |
| Ser | Leu | Glu | Pro<br>20 | Pro | Asp | Ser | Thr | His<br>25 | His | Gly | Gly | Phe | Pro<br>30 | Ala | Ser |
| Gln | Thr | Pro<br>35 | Asn | Lys | Thr | Ala | Ala<br>40 | Pro | Asp | Thr | His | Arg<br>45 | Thr | Pro | Ser |
| Arg | Ser<br>50 | Phe | Gly | Thr | Val | Ala<br>55 | Thr | Glu | Pro | Lys | Leu<br>60 | Phe | Gly | Gly | Phe |
| Asn<br>65 | Thr | Ser | Asp | Thr | Val<br>70 | Thr | Ser | Pro | Gln | Arg<br>75 | Ala | Gly | Ala | Leu | Ala<br>80 |
| Gly | Gly | Val | Thr | Thr<br>85 | Phe | Val | Ala | Leu | Tyr<br>90 | Asp | Tyr | Glu | Ser | Arg<br>95 | Thr |
| Glu | Thr | Asp | Leu<br>100 | Ser | Phe | Lys | Lys | Gly<br>105 | Glu | Arg | Leu | Gln | Ile<br>110 | Val | Asn |
| Asn | Thr | Glu<br>115 | Gly | Asp | Trp | Trp | Leu<br>120 | Ala | His | Ser | Leu | Thr<br>125 | Thr | Gly | Gln |
| Thr | Gly | Tyr | Ile | Pro | Ser | Asn | Tyr | Val | Ala | Pro | Ser | Asp | Ser | Ile | Gln |

|     |     |     | 130 |     |     |     |     | 135 |     |     |     |     | 140 |     |     |
| --- | --- | --- | --- | --- | --- | --- | --- | --- | --- | --- | --- | --- | --- | --- | --- |
| Ala | Glu | Glu | Trp | Tyr | Phe | Gly | Lys | Ile | Thr | Arg | Arg | Glu | Ser | Glu | Arg |
| 145 |     |     |     |     | 150 |     |     |     |     | 155 |     |     |     |     | 160 |
| Leu | Leu | Leu | Asn | Pro | Glu | Asn | Pro | Arg | Gly | Thr | Phe | Leu | Val | Arg | Glu |
|     |     |     |     | 165 |     |     |     |     | 170 |     |     |     |     | 175 |     |
|     | Ser | Glu | Thr | Thr | Lys | Gly | Ala | Tyr | Cys | Leu | Ser | Val | Ser | Asp | Phe | Asp |
|     |     |     | 180 |     |     |     |     | 185 |     |     |     |     | 190 |     |     |
| Asn | Ala | Lys | Gly | Leu | Asn | Val | Lys | His | Tyr | Lys | Ile | Arg | Lys | Leu | Asp |
|     |     | 195 |     |     |     |     | 200 |     |     |     |     | 205 |     |     |     |
| Ser | Gly | Gly | Phe | Tyr | Ile | Thr | Ser | Arg | Thr | Gln | Phe | Ser | Ser | Leu | Gln |
|     | 210 |     |     |     |     | 215 |     |     |     |     | 220 |     |     |     |     |
| Gln | Leu | Val | Ala | Tyr | Tyr | Ser | Lys | His | Ala | Asp | Gly | Leu | Cys | His | Arg |
| 225 |     |     |     | 230 |     |     |     |     | 235 |     |     |     |     |     | 240 |
| Leu | Thr | Asn | Val | Cys | Pro | Thr | Ser | Lys | Pro | Gln | Thr | Gln | Gly | Leu | Ala |
|     |     |     |     | 245 |     |     |     |     | 250 |     |     |     |     | 255 |     |
| Lys | Asp | Ala | Trp | Glu | Ile | Pro | Arg | Glu | Ser | Leu | Arg | Leu | Glu | Val | Lys |
|     |     |     | 260 |     |     |     |     | 265 |     |     |     |     | 270 |     |     |
| Leu | Gly | Gln | Gly | Cys | Phe | Gly | Glu | Val | Trp | Met | Gly | Thr | Trp | Asn | Gly |
|     |     | 275 |     |     |     |     | 280 |     |     |     |     | 285 |     |     |     |
| Thr | Thr | Arg | Val | Ala | Ile | Lys | Thr | Leu | Lys | Pro | Gly | Thr | Met | Ser | Pro |
|     | 290 |     |     |     |     | 295 |     |     |     |     | 300 |     |     |     |     |
| Glu | Ala | Phe | Leu | Gln | Glu | Ala | Gln | Val | Met | Lys | Lys | Leu | Arg | His | Glu |
| 305 |     |     |     | 310 |     |     |     |     | 315 |     |     |     |     |     | 320 |
| Lys | Leu | Val | Gln | Leu | Tyr | Ala | Val | Val | Ser | Glu | Glu | Pro | Ile | Tyr | Ile |
|     |     |     |     | 325 |     |     |     |     | 330 |     |     |     |     | 335 |     |
| Val | Thr | Glu | Tyr | Met | Ser | Lys | Gly | Ser | Leu | Leu | Asp | Phe | Leu | Lys | Gly |
|     |     |     | 340 |     |     |     |     | 345 |     |     |     |     | 350 |     |     |
| Glu | Met | Gly | Lys | Tyr | Leu | Arg | Leu | Pro | Gln | Leu | Val | Asp | Met | Ala | Ala |
|     |     |     | 355 |     |     |     |     | 360 |     |     |     |     | 365 |     |     |
|     | Gln | Ile | Ala | Ser | Gly | Met | Ala | Tyr | Val | Glu | Arg | Met | Asn | Tyr | Val | His |
|     |     |     | 370 |     |     |     |     | 375 |     |     |     |     | 380 |     |     |
| Arg | Asp | Leu | Arg | Ala | Ala | Asn | Ile | Leu | Val | Gly | Glu | Asn | Leu | Val | Cys |
| 385 |     |     |     |     | 390 |     |     |     |     | 395 |     |     |     |     | 400 |
| Lys | Val | Ala | Asp | Phe | Gly | Leu | Ala | Arg | Leu | Ile | Glu | Asp | Asn | Glu | Tyr |
|     |     |     |     | 405 |     |     |     |     | 410 |     |     |     |     | 415 |     |
| Thr | Ala | Arg | Gln | Gly | Ala | Lys | Phe | Pro | Ile | Lys | Trp | Thr | Ala | Pro | Glu |
|     |     |     | 420 |     |     |     |     | 425 |     |     |     |     | 430 |     |     |
| Ala | Ala | Leu | Tyr | Gly | Arg | Phe | Thr | Ile | Lys | Ser | Asp | Val | Trp | Ser | Phe |
|     |     |     | 435 |     |     |     |     | 440 |     |     |     |     | 445 |     |     |
| Gly | Ile | Leu | Leu | Thr | Glu | Leu | Thr | Thr | Lys | Gly | Arg | Val | Pro | Tyr | Pro |
|     |     |     | 450 |     |     |     |     | 455 |     |     |     |     | 460 |     |     |
| Gly | Met | Val | Asn | Arg | Glu | Val | Leu | Asp | Gln | Val | Glu | Arg | Gly | Tyr | Arg |
| 465 |     |     |     |     | 470 |     |     |     |     | 475 |     |     |     |     | 480 |
| Met | Pro | Cys | Pro | Pro | Glu | Cys | Pro | Glu | Ser | Leu | His | Asp | Leu | Met | Cys |
|     |     |     |     | 485 |     |     |     |     | 490 |     |     |     |     | 495 |     |
| Gln | Cys | Trp | Arg | Arg | Asp | Pro | Glu | Glu | Arg | Pro | Thr | Phe | Glu | Tyr | Leu |
|     |     |     |     | 500 |     |     |     |     | 505 |     |     |     |     | 510 |     |
| Gln | Ala | Phe | Leu | Glu | Asp | Tyr | Phe | Thr | Ser | Thr | Glu | Pro | Glu | Tyr | Gln |
|     |     |     | 515 |     |     |     |     | 520 |     |     |     |     | 525 |     |     |
| Pro | Gly | Glu | Asn | Leu |
|     |     |     | 530 |     |

( 2 ) INFORMATION FOR SEQ ID NO:3:

( i ) SEQUENCE CHARACTERISTICS:
        ( A ) LENGTH: 1611

(B) TYPE: Nucleic Acid
(C) STRANDEDNESS: Double
(D) TOPOLOGY: Linear (ii) MOLECULE TYPE: cDNA to mRNA (iii) HYPOTHETICAL: No (iv) ANTI-SENSE: No (vi) ORIGINAL SOURCE:
(A) ORGANISM: Homo sapien (viii) POSITION IN GENOME:
(A) CHROMOSOME/SEGMENT: Chromosome 20

(x) PUBLICATION INFORMATION:
(A) AUTHORS: Anderson, Stephen K.
Gibbs, Carol P.
Tanaka, Akio
Kung, Hsing-Jien
Fujita, Donald J.
(B) TITLE: Human Cellular src Gene:
Nucleotide Sequence and Derived Amino
Acid Sequence of the Region Coding for
the Carboxy-Terminal Two-Thirds of
pp60c-src
(C) JOURNAL: Molecular and Cellular Biology
(D) VOLUME: 5
(E) ISSUE: 5
(F) PAGES: 1122-1129
(G) DATE: May, 1985

(x) PUBLICATION INFORMATION:
(A) AUTHORS: Tanaka, Akio
Gibbs, Carol P.
Arthur, Richard R.
Anderson, Stephen K.
Kung, Hsing-Jien
Fujita, Donald J.
(B) TITLE: DNA Sequence Encoding the
Amino-Terminal Region of the Human c-src
Protein: Implications of Sequence
Divergence among src-Type Kinase
Oncogenes
(C) JOURNAL: Molecular and Cellular Biology
(D) VOLUME: 7
(E) ISSUE: 5
(F) PAGES: 1978-1983
(G) DATE: May, 1987

(xi) SEQUENCE DESCRIPTION: SEQ ID NO:3:

```
ATG GGT AGC AAC AAG AGC AAG CCC AAG GAT GCC AGC CAG CGG CGC CGC        48
Met Gly Ser Asn Lys Ser Lys Pro Lys Asp Ala Ser Gln Arg Arg Arg
                  5                  10                  15

AGC CTG GAG CCC GCC GAG AAC GTG CAC GGC GCT GGC GGG GGC GCT TTC        96
Ser Leu Glu Pro Ala Glu Asn Val His Gly Ala Gly Gly Gly Ala Phe
             20                  25                  30

CCC GCC TCG CAG ACC CCC AGC AAG CCA GCC TCG GCC GAC GGC CAC CGC       144
Pro Ala Ser Gln Thr Pro Ser Lys Pro Ala Ser Ala Asp Gly His Arg
         35                  40                  45

GGC CCC AGC GCG GCC TTC GCC CCC GCG GCC GCC GAG CCC AAG CTG TTC       192
Gly Pro Ser Ala Ala Phe Ala Pro Ala Ala Ala Glu Pro Lys Leu Phe
     50                  55                  60

GGA GGC TTC AAC TCC TCG GAC ACC GTC ACC TCC CCG CAG AGG GCG GGC       240
Gly Gly Phe Asn Ser Ser Asp Thr Val Thr Ser Pro Gln Arg Ala Gly
 65                  70                  75                  80

CCG CTG GCC GGT GGA GTG ACC ACC TTT GTG GCC CTC TAT GAC TAT GAG       288
Pro Leu Ala Gly Gly Val Thr Thr Phe Val Ala Leu Tyr Asp Tyr Glu
                     85                  90                  95

TCT AGG ACG GAG ACA GAC CTG TCC TTC AAG AAA GGC GAG CGG CTC CAG       336
Ser Arg Thr Glu Thr Asp Leu Ser Phe Lys Lys Gly Glu Arg Leu Gln
                100                 105                 110

ATT GTC AAC AAC ACA GAG GGA GAC TGG TGG CTG GCC CAC TCG CTC AGC       384
```

| | | | | | | | | | | | | | | | | |
|---|---|---|---|---|---|---|---|---|---|---|---|---|---|---|---|---|
| Ile | Val | Asn | Asn | Thr | Glu | Gly | Asp | Trp | Trp | Leu | Ala | His | Ser | Leu | Ser | |
| | 115 | | | | 120 | | | | | 125 | | | | | | |
| ACA | GGA | CAG | ACA | GGC | TAC | ATC | CCC | AGC | AAC | TAC | GTG | GCG | CCC | TCC | GAC | 432 |
| Thr | Gly | Gln | Thr | Gly | Tyr | Ile | Pro | Ser | Asn | Tyr | Val | Ala | Pro | Ser | Asp | |
| | 130 | | | | 135 | | | | | 140 | | | | | | |
| TCC | ATC | CAG | GCT | GAG | GAG | TGG | TAT | TTT | GGC | AAG | ATC | ACC | AGA | CGG | GAG | 480 |
| Ser | Ile | Gln | Ala | Glu | Glu | Trp | Tyr | Phe | Gly | Lys | Ile | Thr | Arg | Arg | Glu | |
| 145 | | | | | 150 | | | | | 155 | | | | | 160 | |
| TCA | GAG | CGG | TTA | CTG | CTC | AAT | GCA | GAG | AAC | CCG | AGA | GGG | ACC | TTC | CTC | 528 |
| Ser | Glu | Arg | Leu | Leu | Leu | Asn | Ala | Glu | Asn | Pro | Arg | Gly | Thr | Phe | Leu | |
| | | | | 165 | | | | | 170 | | | | | 175 | | |
| GTG | CGA | GAA | AGT | GAG | ACC | ACG | AAA | GGT | GCC | TAC | TGC | CTC | TCA | GTG | TCT | 576 |
| Val | Arg | Glu | Ser | Glu | Thr | Thr | Lys | Gly | Ala | Tyr | Cys | Leu | Ser | Val | Ser | |
| | | | 180 | | | | | 185 | | | | | 190 | | | |
| GAC | TTC | GAC | AAC | GCC | AAG | GGC | CTC | AAC | GTG | AAG | CAC | TAC | AAG | ATC | CGC | 624 |
| Asp | Phe | Asp | Asn | Ala | Lys | Gly | Leu | Asn | Val | Lys | His | Tyr | Lys | Ile | Arg | |
| | | 195 | | | | | 200 | | | | | 205 | | | | |
| AAG | CTG | GAC | AGC | GGC | GGC | TTC | TAC | ATC | ACC | TCC | CGC | ACC | CAG | TTC | AAC | 672 |
| Lys | Leu | Asp | Ser | Gly | Gly | Phe | Tyr | Ile | Thr | Ser | Arg | Thr | Gln | Phe | Asn | |
| | 210 | | | | | 215 | | | | | 220 | | | | | |
| AGC | CTG | CAG | CAG | CTG | GTG | GCC | TAC | TAC | TCC | AAA | CAC | GCC | GAT | GGC | CTG | 720 |
| Ser | Leu | Gln | Gln | Leu | Val | Ala | Tyr | Tyr | Ser | Lys | His | Ala | Asp | Gly | Leu | |
| 225 | | | | | 230 | | | | | 235 | | | | | 240 | |
| TGC | CAC | CGC | CTC | ACC | ACC | GTG | TGC | CCC | ACG | TCC | AAG | CCG | CAG | ACT | CAG | 768 |
| Cys | His | Arg | Leu | Thr | Thr | Val | Cys | Pro | Thr | Ser | Lys | Pro | Gln | Thr | Gln | |
| | | | | 245 | | | | | 250 | | | | | 255 | | |
| GGC | CTG | GCC | AAG | GAT | GCC | TGG | GAG | ATC | CCT | CGG | GAG | TCG | CTG | CGG | CTG | 816 |
| Gly | Leu | Ala | Lys | Asp | Ala | Trp | Glu | Ile | Pro | Arg | Glu | Ser | Leu | Arg | Leu | |
| | | | 260 | | | | | 265 | | | | | 270 | | | |
| GAG | GTC | AAG | CTG | GGC | CAG | GGC | TGC | TTT | GGC | GAG | GTG | TGG | ATG | GGG | ACC | 864 |
| Glu | Val | Lys | Leu | Gly | Gln | Gly | Cys | Phe | Gly | Glu | Val | Trp | Met | Gly | Thr | |
| | | 275 | | | | | 280 | | | | | 285 | | | | |
| TGG | AAC | GGT | ACC | ACC | AGG | GTG | GCC | ATC | AAA | ACC | CTG | AAG | CCT | GGC | ACG | 912 |
| Trp | Asn | Gly | Thr | Thr | Arg | Val | Ala | Ile | Lys | Thr | Leu | Lys | Pro | Gly | Thr | |
| | 290 | | | | | 295 | | | | | 300 | | | | | |
| ATG | TCT | CCA | GAG | GCC | TTC | CTG | CAG | GAG | GCC | CAG | GTC | ATG | AAG | AAG | CTG | 960 |
| Met | Ser | Pro | Glu | Ala | Phe | Leu | Gln | Glu | Ala | Gln | Val | Met | Lys | Lys | Leu | |
| 305 | | | | | 310 | | | | | 315 | | | | | 320 | |
| AGG | CAT | GAG | AAG | CTG | GTG | CAG | TTG | TAT | GCT | GTG | GTT | TCA | GAG | GAG | CCC | 1008 |
| Arg | His | Glu | Lys | Leu | Val | Gln | Leu | Tyr | Ala | Val | Val | Ser | Glu | Glu | Pro | |
| | | | | 325 | | | | | 330 | | | | | 335 | | |
| ATT | TAC | ATC | GTC | ACG | GAG | TAC | ATG | AGC | AAG | GGG | AGT | TTG | CTG | GAC | TTT | 1056 |
| Ile | Tyr | Ile | Val | Thr | Glu | Tyr | Met | Ser | Lys | Gly | Ser | Leu | Leu | Asp | Phe | |
| | | | 340 | | | | | 345 | | | | | 350 | | | |
| CTC | AAG | GGG | GAG | ACA | GGC | AAG | TAC | CTG | CGG | CTG | CCT | CAG | CTG | GTG | GAC | 1104 |
| Leu | Lys | Gly | Glu | Thr | Gly | Lys | Tyr | Leu | Arg | Leu | Pro | Gln | Leu | Val | Asp | |
| | | 355 | | | | | 360 | | | | | 365 | | | | |
| ATG | GCT | GCT | CAG | ATC | GCC | TCA | GGC | ATG | GCG | TAC | GTG | GAG | CGG | ATG | AAC | 1152 |
| Met | Ala | Ala | Gln | Ile | Ala | Ser | Gly | Met | Ala | Tyr | Val | Glu | Arg | Met | Asn | |
| | 370 | | | | 375 | | | | | 380 | | | | | | |
| TAC | GTC | CAC | CGG | GAC | CTT | CGT | GCA | GCC | AAC | ATC | CTG | GTG | GGA | GAG | AAC | 1200 |
| Tyr | Val | His | Arg | Asp | Leu | Arg | Ala | Ala | Asn | Ile | Leu | Val | Gly | Glu | Asn | |
| 385 | | | | | 390 | | | | | 395 | | | | | 400 | |
| CTG | GTG | TGC | AAA | GTG | GCC | GAC | TTT | GGG | CTG | GCT | CGG | CTC | ATT | GAA | GAC | 1248 |
| Leu | Val | Cys | Lys | Val | Ala | Asp | Phe | Gly | Leu | Ala | Arg | Leu | Ile | Glu | Asp | |
| | | | 405 | | | | | 410 | | | | | 415 | | | |
| AAT | GAG | TAC | ACG | GCG | CGG | CAA | GGT | GCC | AAA | TTC | CCC | ATC | AAG | TGG | ACG | 1296 |
| Asn | Glu | Tyr | Thr | Ala | Arg | Gln | Gly | Ala | Lys | Phe | Pro | Ile | Lys | Trp | Thr | |
| | | | 420 | | | | | 425 | | | | | 430 | | | |
| GCT | CCA | GAA | GCT | GCC | CTC | TAT | GGC | CGC | TTC | ACC | ATC | AAG | TCG | GAC | GTG | 1344 |
| Ala | Pro | Glu | Ala | Ala | Leu | Tyr | Gly | Arg | Phe | Thr | Ile | Lys | Ser | Asp | Val | |
| | | 435 | | | | | 440 | | | | | 445 | | | | |

| | | | | | | | | | | | | | | | | |
|---|---|---|---|---|---|---|---|---|---|---|---|---|---|---|---|---|
| TGG | TCC | TTC | GGG | ATC | CTG | CTG | ACT | GAG | CTC | ACC | ACA | AAG | GGA | CGG | GTG | 1392 |
| Trp | Ser | Phe | Gly | Ile | Leu | Leu | Thr | Glu | Leu | Thr | Thr | Lys | Gly | Arg | Val | |
| | 450 | | | | | 455 | | | | | 460 | | | | | |
| CCC | TAC | CCT | GGG | ATG | GTG | AAC | CGC | GAG | GTG | CTG | GAC | CAG | GTG | GAG | CGG | 1440 |
| Pro | Tyr | Pro | Gly | Met | Val | Asn | Arg | Glu | Val | Leu | Asp | Gln | Val | Glu | Arg | |
| 465 | | | | | 470 | | | | | 475 | | | | | 480 | |
| GGC | TAC | CGG | ATG | CCC | TGC | CCG | CCG | GAG | TGT | CCC | GAG | TCC | CTG | CAC | GAC | 1488 |
| Gly | Tyr | Arg | Met | Pro | Cys | Pro | Pro | Glu | Cys | Pro | Glu | Ser | Leu | His | Asp | |
| | | | | 485 | | | | | 490 | | | | | 495 | | |
| CTC | ATG | TGC | CAG | TGC | TGG | CGG | AAG | GAG | CCT | GAG | GAG | CGG | CCC | ACC | TTC | 1536 |
| Leu | Met | Cys | Gln | Cys | Trp | Arg | Lys | Glu | Pro | Glu | Glu | Arg | Pro | Thr | Phe | |
| | | | 500 | | | | | 505 | | | | | 510 | | | |
| GAG | TAC | CTG | CAG | GCC | TTC | CTG | GAG | GAC | TAC | TTC | ACG | TCC | ACC | GAG | CCC | 1584 |
| Glu | Tyr | Leu | Gln | Ala | Phe | Leu | Glu | Asp | Tyr | Phe | Thr | Ser | Thr | Glu | Pro | |
| | | 515 | | | | | 520 | | | | | 525 | | | | |
| CAG | TAC | CAG | CCC | GGG | GAG | AAC | CTC | TAG | | | | | | | | 1611 |
| Gln | Tyr | Gln | Pro | Gly | Glu | Asn | Leu | | | | | | | | | |
| | | 530 | | | | 535 | | | | | | | | | | |

(2) INFORMATION FOR SEQ ID NO:4:

(i) SEQUENCE CHARACTERISTICS:
        (A) LENGTH: 536 amino acids
        (B) TYPE: Amino Acid
        (D) TOPOLOGY: Linear (ii) MOLECULE TYPE: Protein (iii) HYPOTHETICAL: No (v) FRAGMENT TYPE: Complete Sequence (vi) ORIGINAL SOURCE:
        (A) ORGANISM: Homo sapien (x) PUBLICATION INFORMATION:
        (A) AUTHORS: Anderson, Stephen K.
                Gibbs, Carol P.
                Tanaka, Akio
                Kung, Hsing- Jien
                Fujita, Donald J.
        (B) TITLE: Human Cellular src Gene:
                Nucleotide Sequence and Derived Amino
                Acid Sequence of the Region Coding for
                the Carboxy- Terminal Two-Thirds of
                pp60c- src
        (C) JOURNAL: Molecular and Cellular Biology
        (D) VOLUME: 5
        (E) ISSUE: 5
        (F) PAGES: 1122-1129
        (G) DATE: May, 1985

(x) PUBLICATION INFORMATION:
        (A) AUTHORS: Tanaka, Akio
                Gibbs, Carol P.
                Arthur, Richard R.
                Anderson, Stephen K.
                Kung, Hsing- Jien
                Fujita, Donald J.
        (B) TITLE: DNA Sequence Encoding the
                Amino- Terminal Region of the Human c-src
                Protein: Implications of Sequence
                Divergence among src-Type Kinase
                Oncogenes
        (C) JOURNAL: Molecular and Cellular Biology
        (D) VOLUME: 7
        (E) ISSUE: 5
        (F) PAGES: 1978-1983
        (G) DATE: May, 1987

(xi) SEQUENCE DESCRIPTION: SEQ ID NO:4:

| | | | | | | | | | | | | | | |
|---|---|---|---|---|---|---|---|---|---|---|---|---|---|---|
| Met | Gly | Ser | Asn | Lys | Ser | Lys | Pro | Lys | Asp | Ala | Ser | Gln | Arg | Arg |
| | | | | 5 | | | | | 10 | | | | | 15 |

-continued

```
Ser  Leu  Glu  Pro  Ala  Glu  Asn  Val  His  Gly  Ala  Gly  Gly  Gly  Ala  Phe
               20                      25                     30

Pro  Ala  Ser  Gln  Thr  Pro  Ser  Lys  Pro  Ala  Ser  Ala  Asp  Gly  His  Arg
               35                      40                     45

Gly  Pro  Ser  Ala  Ala  Phe  Ala  Pro  Ala  Ala  Ala  Glu  Pro  Lys  Leu  Phe
               50                      55                     60

Gly  Gly  Phe  Asn  Ser  Ser  Asp  Thr  Val  Thr  Ser  Pro  Gln  Arg  Ala  Gly
 65                      70                      75                          80

Pro  Leu  Ala  Gly  Gly  Val  Thr  Thr  Phe  Val  Ala  Leu  Tyr  Asp  Tyr  Glu
                         85                      90                     95

Ser  Arg  Thr  Glu  Thr  Asp  Leu  Ser  Phe  Lys  Lys  Gly  Glu  Arg  Leu  Gln
               100                     105                    110

Ile  Val  Asn  Asn  Thr  Glu  Gly  Asp  Trp  Trp  Leu  Ala  His  Ser  Leu  Ser
               115                     120                    125

Thr  Gly  Gln  Thr  Gly  Tyr  Ile  Pro  Ser  Asn  Tyr  Val  Ala  Pro  Ser  Asp
               130                     135                    140

Ser  Ile  Gln  Ala  Glu  Glu  Trp  Tyr  Phe  Gly  Lys  Ile  Thr  Arg  Arg  Glu
145                          150                     155                    160

Ser  Glu  Arg  Leu  Leu  Leu  Asn  Ala  Glu  Asn  Pro  Arg  Gly  Thr  Phe  Leu
               165                     170                    175

Val  Arg  Glu  Ser  Glu  Thr  Thr  Lys  Gly  Ala  Tyr  Cys  Leu  Ser  Val  Ser
                    180                     185                    190

Asp  Phe  Asp  Asn  Ala  Lys  Gly  Leu  Asn  Val  Lys  His  Tyr  Lys  Ile  Arg
               195                     200                    205

Lys  Leu  Asp  Ser  Gly  Gly  Phe  Tyr  Ile  Thr  Ser  Arg  Thr  Gln  Phe  Asn
               210                     215                    220

Ser  Leu  Gln  Gln  Leu  Val  Ala  Tyr  Tyr  Ser  Lys  His  Ala  Asp  Gly  Leu
225                          230                     235                    240

Cys  His  Arg  Leu  Thr  Thr  Val  Cys  Pro  Thr  Ser  Lys  Pro  Gln  Thr  Gln
               245                     250                    255

Gly  Leu  Ala  Lys  Asp  Ala  Trp  Glu  Ile  Pro  Arg  Glu  Ser  Leu  Arg  Leu
               260                     265                    270

Glu  Val  Lys  Leu  Gly  Gln  Gly  Cys  Phe  Gly  Glu  Val  Trp  Met  Gly  Thr
               275                     280                    285

Trp  Asn  Gly  Thr  Thr  Arg  Val  Ala  Ile  Lys  Thr  Leu  Lys  Pro  Gly  Thr
290                          295                     300

Met  Ser  Pro  Glu  Ala  Phe  Leu  Gln  Glu  Ala  Gln  Val  Met  Lys  Lys  Leu
305                          310                     315                    320

Arg  His  Glu  Lys  Leu  Val  Gln  Leu  Tyr  Ala  Val  Val  Ser  Glu  Glu  Pro
               325                     330                    335

Ile  Tyr  Ile  Val  Thr  Glu  Tyr  Met  Ser  Lys  Gly  Ser  Leu  Leu  Asp  Phe
               340                     345                    350

Leu  Lys  Gly  Glu  Thr  Gly  Lys  Tyr  Leu  Arg  Leu  Pro  Gln  Leu  Val  Asp
               355                     360                    365

Met  Ala  Ala  Gln  Ile  Ala  Ser  Gly  Met  Ala  Tyr  Val  Glu  Arg  Met  Asn
                    370                     375                    380

Tyr  Val  His  Arg  Asp  Leu  Arg  Ala  Ala  Asn  Ile  Leu  Val  Gly  Glu  Asn
385                          390                     395                    400

Leu  Val  Cys  Lys  Val  Ala  Asp  Phe  Gly  Leu  Ala  Arg  Leu  Ile  Glu  Asp
               405                     410                    415

Asn  Glu  Tyr  Thr  Ala  Arg  Gln  Gly  Ala  Lys  Phe  Pro  Ile  Lys  Trp  Thr
               420                     425                    430

Ala  Pro  Glu  Ala  Ala  Leu  Tyr  Gly  Arg  Phe  Thr  Ile  Lys  Ser  Asp  Val
               435                     440                    445

Trp  Ser  Phe  Gly  Ile  Leu  Leu  Thr  Glu  Leu  Thr  Thr  Lys  Gly  Arg  Val
```

|  | 450 |  |  |  |  | 455 |  |  |  |  | 460 |  |  |  |
|---|---|---|---|---|---|---|---|---|---|---|---|---|---|---|
| Pro 465 | Tyr | Pro | Gly | Met | Val 470 | Asn | Arg | Glu | Val | Leu 475 | Asp | Gln | Val | Glu Arg 480 |
| Gly | Tyr | Arg | Met | Pro 485 | Cys | Pro | Pro | Glu | Cys 490 | Pro | Glu | Ser | Leu | His Asp 495 |
| Leu | Met | Cys | Gln 500 | Cys | Trp | Arg | Lys | Glu 505 | Pro | Glu | Glu | Arg | Pro 510 | Thr Phe |
| Glu | Tyr | Leu 515 | Gln | Ala | Phe | Leu | Glu 520 | Asp | Tyr | Phe | Thr | Ser 525 | Thr | Glu Pro |
| Gln | Tyr 530 | Gln | Pro | Gly | Glu | Asn 535 | Leu |  |  |  |  |  |  |  |

GENETICALLY ENGINEERED ENDOTHELIAL CELLS EXHIBITING ENHANCED MIGRATION AND PLASMINOGEN ACTIVATOR ACTIVITY

The U.S. Government has a paid-up license in this invention and the right in limited circumstances to require the patent owner to license others on reasonable terms as provided for by the terms of Grants Nos. 5K11-HL02351, RO1-HL28373, and 9T32 DKO7556 awarded by The National Institutes of Health, Bethesda, Md.

FIELD OF THE INVENTION

This invention relates to genetically engineered endothelial cells and, in particular, to genetically engineered endothelial cells which exhibit enhanced migration and enhanced plasminogen activator activity.

BACKGROUND OF THE INVENTION

Endothelial cells are specialized cells which form the lining of the heart and the blood vessels. Because of their direct contact with the circulating blood, a number of proposals have been made to genetically engineer these cells and use them as "in vivo" drug delivery systems. See, for example, Culliton, B. J. 1989. "Designing Cells to Deliver Drugs," *Science.* 246:746-751; and Zwiebel, J. A., S. M. Freeman, P. W. Kantoff, K. Cornetta, U. S. Ryan, and W. F. Anderson. 1989. "High-Level Recombinant Gene Expression in Rabbit Endothelial Cells Transduced by Retroviral Vectors," *Science.* 243:220-222 (transfer of a human adenosine deaminase gene and a rat growth hormone gene to aortic endothelial cells using a retroviral vector and demonstration of the secretion of rat growth hormone from such cells after seeding onto a synthetic vascular graft).

Endothelial cells are known to play an important role in the pathogenesis of atherosclerotic plaques, as well as in the success or failure of various surgical procedures, including vascular stent implantation, coronary angioplasty, and coronary bypass surgery using autologous veins or arteries or synthetic materials, such as, dacron or expanded polytetrafluorethylene.

Endothelial cells affect both the disease process and efforts to reconstruct damaged vessels because, among other things, they can: 1) alter the thrombogenic properties of the blood vessel wall, 2) modulate smooth muscle cell proliferation and migration, and 3) affect vascular smooth muscle tone through multiple pathways including the renin-angiotensin system (i.e., the system wherein the proteolytic enzyme renin cleaves two amino acids from angiotensin I to produce the hypertensive agent angiotensin II).

With regard to their interaction with the renin-angiotensin system, investigators have demonstrated in vitro that many of the constituents of that system, including angiotensinogen, renin, angiotensin-converting enzyme, and angiotensin II receptors, are contained within endothelial cells thus forming an autocrine angiotensin system. See Lilly, L. S., R. E. Pratt, R. W. Alexander, D. M. Larson, K. E. Ellison, M. A. Gimbrone, and V. J. Dzau. 1985. "Renin expression by vascular endothelial cells in culture," *Circ. Res.* 57:312-318; Caldwell, P. R. B., B. C. Seegal, and K. C. Hsu. 1976. "Angiotensin-converting enzyme: vascular endothelial localization," *Science (Wash. D.C.).* 191:1050-1051; Ryan, U. S., J. W. Ryan, C. Whitaker, and A. Chiu. 1976. "Localization of angiotensin converting enzyme (kininase II). II. Immunocytochemistry and immunofluorescence," *Tissue Cell.* 8:125-145; Johnson, A. R., and E. G. Erdos. 1977. "Metabolism of vasoactive peptides by human endothelial cells in culture: angiotensin I converting enzyme (kininase II) and angiotensinase," *J. Clin. Invest.* 59:684-695; and Patel, J. M., F. R. Yarid, E. R. Block, and M. K. Raizda. 1989. "Angiotensin receptors in pulmonary arterial and aortic endothelial cells," *Am. J. Physiol* 256:C987-C993. Also, interruption of the endothelial autocrine angiotensin system, with either the angiotensin-converting enzyme inhibitor lisinopril or the angiotensin II receptor antagonist sar$^1$, ile$^8$-angiotensin II, has been shown to lead to increased endothelial cell migration and urokinase-like plasminogen activator (u-PA) activity. See Bell, L. and J. A. Madri. 1990. "Influence of the angiotensin system on endothelial and smooth muscle cell migration," *Am. J. Pathol.* 137:7-12.

In terms of clinical practice, restenosis following coronary angioplasty comprises a significant medical problem since it occurs within six months following 30-50% of the procedures performed and is associated with substantial patient morbidity and health care expenditures. All angioplasties cause removal of the endothelial cell lining of the blood vessel. The principal reasons for the restenosis are acute thrombus formation due to loss of the anti-thrombotic surface provided by the endothelial cells and neointima formation due to unchecked smooth muscle cell stimulation by blood-borne cells, again due to the loss of the protective endothelial cell layer.

For example, Fishman, J. A., G. B. Ryan, M. J. Karnovsky. 1975. "Endothelial regeneration in the rat carotid artery and the significance of endothelial denudation in the pathogenesis of myointimal thickening," *Laboratory Investigation.* 32:339-351 show that loss of endothelial cells with denudation injury to the blood vessel wall is correlated with the subsequent formation of a neointima, or ingrowth of smooth muscle cells from the media into the intima and elaboration of increased amount of extracellular matrix material resulting in a new intima. Schwartz, S. M., C. C. Haudenschild, and E. M. Eddy. 1978. "Endothelial regeneration: I. Quantitative analysis of initial stages of endothelial regeneration in rat aortic intima," *Laboratory Investigation.* 38:568-580 show that following denudation injury to an artery, in vivo, as would be expected following angioplasty or saphenous vein graft harvesting, remaining endothelial cells migrate to restore luminal integrity, and further Haudenschild, C. C. and S. M. Schwartz. 1979. "Endothelial regeneration: II. Restitution of endothelial continuity," *Laboratory Investigation.* 41:407-418 show that injured vessel areas which are rapidly covered by a continuous layer of endothelium are protected from the development of neointima formation, or vessel lumen occlusion. Reidy, M. A. and S. M. Schwartz. 1981. "Endothelial regeneration: III. Time course of intimal changes after small defined injury to rat aortic endothelium," *Laboratory Investigation.* 44:301-308 also show that rapid coverage of the injured area is beneficial since removal of only a small number of endothelial cells from the vessel lumen allows rapid recoverage of the area with endothelial cells and prevents the development of neointima formation, or vessel lumen occlusion. Further, Madri, J. A., M. A. Reidy, O. Kocher, and L. Bell. 1989. "Endothelial cell behavior following denudation injury is modulated by TGF-B1 and fibronectin," *Laboratory Investigation.*

60:755–765 show that changes in in vivo endothelial cell migration correlate with in vitro endothelial cell migration assays. Hence, rapid coverage of a denuded vessel segment, after angioplasty or following saphenous vein harvesting for bypass surgery for example, is an important parameter in preventing the vessel occlusion that commonly follows these procedures.

Occlusion of peripheral arterial and coronary artery bypass grafts is a further frequent and important clinical finding. Two-thirds of the saphenous vein coronary bypass grafts are either severely diseased or entirely occluded by six to eleven years following bypass surgery. Peripheral arterial bypass grafts have a similar fate. The occlusion is due to loss of endothelial cells from the surface of the vein graft during harvesting of the graft and at the time of initial surgery.

Synthetic grafts also exhibit high rates of occlusion. Initially, grafts of this type are not endothelialized. This results in a substantial incidence of early occlusion due to thrombosis. With time, the grafts become partially re-endothelialized by migration of arterial endothelial cells from the proximal and distal anastomotic sites or from ingrowth of capillary endothelial cells through the porous synthetic graft onto the luminal surface. However, the process of endothelial cell migration is normally slow and does not permit total coverage of the graft by arterial endothelial cells. Further, ingrowing capillary endothelial cells are less capable of inhibiting clot formation than arterial endothelial cells. Attempts to reseed peripheral grafts with autologous endothelial cells have demonstrated that incomplete coverage of the graft at the time of seeding results in graft closure and lack of clinical benefit of the seeding procedure.

Thus, Zilla, P., R. Fasol, M. Deutsch, T. Fischlein, E. Minar, A. Hammerle, 0. Krapicka, and M. Kadietz. 1987. "Endothelial cell seeding of polytetrafluoroethylene vascular grafts in humans: A preliminary report," *Journal of Vascular Surgery.* 6:535–541 and Fasol, R., P. Zilla, M. Deutsch, M. Grimm, T. Fischlein, and G. Laugfer. 1989. "Human endothelial cell seeding: Evaluation of its effectiveness by platelet parameters after one year," *Journal of Vascular Surgery.* 9:432–436 describe the absence of any significant improvement in platelet factors or function, platelet uptake on the graft surface, or distal blood flow up to one year after peripheral arterial bypass with a synthetic graft in patients who received synthetic grafts only partially coated with autologous endothelial cells. Ortenwall, P., H. Wadevik, J. Kutti, and B. Risberg. 1990. "Endothelial cell seeding reduces thrombogenicity of Dacron grafts in humans," *Journal of Vascular Surgery.* 11:403–410 did not observe any significant improvement in graft patency in patients who received synthetic graft partially coated with autologous endothelial cells. Thus reseeding of synthetic grafts, or autologous grafts or denuded angioplasty sites, with endothelial cells will not result in clinical therapeutic benefit unless there is virtually complete coverage of the vessel segment with a continuous layer of endothelium.

Genetic engineering of endothelial cells has been performed by a number of workers in the art. For example, Nabel, E. G., G. Plautz, F. M. Boyce, J. C. Stanley, and G. J. Nabel. 1989. "Recombinant Gene Expression in Vivo Within Endothelial Cells of the Arterial Wall," *Science.* 244:1342–1343, describe experiments in which a gene for the marker protein $\beta$-galactosidase was transferred to endothelial cells using a retroviral vector and the thus modified cells were seeded onto the walls of an artery in vivo using a double balloon catheter to isolate the section of the artery where the seeding took place. Nabel et al. report that up to four weeks after surgery, the seeded arteries were found to contain endothelial cells which expressed $\beta$-galactosidase.

Wilson, J. M., L. K. Birinyi, R. N. Salomon, P. Libby, A. D. Callow, and R. C. Mulligan. 1989. "Implantation of Vascular Grafts Lined with Genetically Modified Endothelial Cells," *Science.* 244:1344–1346, describe similar work wherein a $\beta$-galactosidase gene was transferred to endothelial cells using a retrovirus, the modified cells were seeded onto synthetic grafts, and the grafts were implanted in the carotid arteries of dogs. Five weeks later, the grafts were removed and found to still contain the genetically modified endothelial cells along their luminal surfaces.

Along these same lines, Dichek, D. A., R. F. Neville, J. A. Zwiebel, S. Freeman, M. B. Leon, and W. F. Anderson. 1989. "Seeding of Intravascular Stents with Genetically Engineered Endothelial Cells," *Circulation.* 80:1347–1353, describe the seeding of stainless steel stents with genetically engineered endothelial cells carrying in some cases a $\beta$-galactosidase gene and in others a human tissue-type plasminogen activator (TPA) gene. See also PCT Patent Publication No. WO 90/06997 (transfer of $\beta$-galactosidase, rat growth hormone, and human adenosine deaminase, CD-4, and TPA genes to endothelial cells and seeding of silicon coated polyurethane grafts and stainless steel stents with genetically engineered cells); and Zweibel et al. 1989, supra.

Direct in vivo transformation of arterial endothelial cells using retroviral particles or plasmid carrying liposomes is described in Nabel, E. G., G. Plautz, and G. J. Nabel. 1990. "Site-Specific Gene Expression in Vivo by Direct Gene Transfer into the Arterial Wall," *Science.* 249:1285–1288. $\beta$-galactosidase was again used as a marker protein, and evidence of transformation could be found 21 weeks after transfection.

The cellular src gene (c-src gene) was first identified in the late 1970's. See Stehelin, D., H. E. Varmus, J. M. Bishop, and P. K. Vogt. 1976. "DNA related to the transforming gene(s) of avian sarcoma viruses is present in normal avian DNA," *Nature.* 260:170–173; and Spector, D., H. E. Varmus, and J. M. Bishop. 1978a. "Nucleotide sequences related to the transforming gene of avian sarcoma virus are present in DNA of uninfected vertebrates," *Proc. Nat. Acad. Sci. USA.* 75:4102–4106. The gene appears to be present in all animal species and is highly conserved. It encodes a 60,000 dalton protein, tyrosine kinase, which is localized on the cytoplasmic side of the plasma membrane. The c-src protein will be designated herein as pp60$^{c\text{-}src}$.

pp60$^{c\text{-}src}$ is a representative molecule of the src-family of membrane-bound tyrosine kinases including, but not limited to yes, lck, and fyn. (See C. A. Koch, D. Anderson, M. F. Moran, C. Ellis, and T. Pawson. 1991 "SH2 and SH3 domains: elements that control interactions of cytoplasmic signaling proteins," *Science.* 252:668–674.) Certain critical and highly conserved noncatalytic domains in the src family of tyrosine kinases are called Src homology (SH) regions 2 and 3 and are involved in protein-protein interactions. These Src-homology domains are also found in a series of critical molecules, including, but not limited to fyn, lck, yes, PLC, p85, tensin, crk, vav, GAP, fps, arg, dabl, hck, blk, fgr, and nck. These domains are believed to regulate various cell effects of src and related molecules including, but not limited to, signal transduction pathways of tyrosine kinase receptors.

The sequence of the c-src gene has been known for some time. See Takeya, T. and H. Hanafusa. 1983. "Structure and Sequence of the Cellular Gene Homologous to the RSV src Gene and the Mechanism for Generating the Transforming Virus," *Cell.* 32:881–890. A copy of the nucleotide sequence for the coding region of this gene in the chicken and of the resulting pp60$^{c-src}$ protein as published by Takeya and Hanafusa appear as SEQ. ID. NOS. 1 and 2, respectively, set forth below. The corresponding human sequences are set forth as SEQ. ID. NOS. 3 and 4. See Anderson, S. K., C. P. Gibbs, A. Tanaka, H. Kung, and D. Fujita. 1985. "Human Cellular src Gene: Nucleotide Sequence and Derived Amino Acid Sequence of the Region Coding for the Carboxy-Terminal Two-Thirds of pp60$^{c-src}$," *Molecular and Cellular Biology.* 5:1122–1129 and Tanaka, A., C. P. Gibbs, R. R. Arthur, S. K. Anderson, H. Kung, and D. Fujita. 1987. "DNA Sequence Encoding the Amino-Terminal Region of the Human c-src Protein: implications of Sequence Divergence among src-Type Kinase Oncogenes," *Molecular and Cellular Biology.* 7:1978–1983.

Various functions and properties of the c-src gene have been described in the literature. For example, Shalloway, D., P. M. Coussens, and P. Yaciuk. 1984. "Overexpression of the C-src Protein Does Not Induce Transformation of NIH 3T3 Cells," *Proc. Natl. Acad. Sci. USA.* 81:7071–7075, have shown that genetically engineered mouse NIH 3T3 fibroblast cells which overexpress pp60$^{c-src}$ are not malignant. Azarnia, R. S. Reddy, T. E. Kmiecik, D. Shalloway, and W. R. Loewenstein. 1988. "The Cellular src Gene Product Regulates Junctional Cell-to-Cell Communication," *Science.* 23:398–401, have shown that overexpression of pp60$^{c-src}$ in NIH 3T3 cells causes a reduction in cell-to-cell transmission of molecules in the 400 to 700 dalton range. See also Loewenstein, W. R., and R. Azarnia. 1988. "Regulation of Intercellular Communication and Growth by the Cellular src Gene," *Annals New York Academy of Sciences.* 551:337–346. Soriano, P., C. Montgomery, R. Geske, and A. Bradley. 1991. "Targeted Disruption of the c-src Proto-Oncogene Leads to Osteopetrosis in Mice," *Cell.* 64:693–702, have shown that mutation of the c-src gene results in a marked decrease in the rate of bone resorption in mice, i.e., osteopetrosis, thus suggesting that the normal c-src gene plays a role in bone formation.

In addition to the foregoing, Warren, S. L., L. M. Handel and W. J. Nelson. 1988. "Elevated expression of pp60$^{c-src}$ alters a selective morphogenetic property of epithelial cells in vitro without a mitogenic effect," *Mol. Cell. Biol.* 8:632–646, have shown that the overexpression of pp60$^{c-src}$ in Madin-Darby canine kidney cells causes those cells to undergo changes in shape, including the formation of elongated cell processes having lengths in the range of 100 to 200 microns.

A gene related to the c-src gene is the oncogene v-src which forms part of the genome of the Rous sarcoma virus and causes that virus to produce sarcomas in chickens. See Takeya and Hanafusa, supra; and Hunter, T. 1987. "A Tail of Two src's: Mutatis Mutandis," *Cell.* 49:1–4. As with many malignant cells, cells infected with the Rous sarcoma virus have been found to exhibit increased production of urokinase-type plasminogen activator (u-PA). In particular, Bell, S. M., R. W. Brackenbury, N. D. Leslie and J. L. Degen. 1990. "Plasminogen activator gene expression is induced by the src oncogene product and tumor promoters," *J. Biol. Chem.* 265:1333–1338, have correlated the increased production of u-PA after transformation of chicken embryo fibroblasts by the Rous sarcoma virus with an increase in cellular u-PA mRNA.

Significantly, none of the foregoing references in any way discloses or suggests the surprising results achieved by the present invention wherein increased expression of pp60$^{c-src}$ by genetically engineered endothelial cells has been found to result in 1) enhanced migration of the cells, i.e., an enhanced ability to repair the endothelial lining of damaged vessels and/or an enhanced ability to form an endothelial lining on grafts or stents; and 2) enhanced urokinase-type plasminogen activator activity, i.e., an enhanced ability to dissolve or prevent the formation of the thrombi normally associated with vascular surgical procedures.

SUMMARY OF THE INVENTION

In view of the foregoing state of the art, it is an object of this invention to provide genetically engineered endothelial cells having improved therapeutic properties. More particularly, it is an object of the invention to provide genetically engineered endothelial cells which migrate at higher rates than corresponding endothelial cells which have not been genetically engineered. It is also an object of the invention to provide genetically engineered endothelial cells which have an enhanced ability to inhibit the formation of thrombi and/or to dissolve thrombi once they have formed.

With regard to clinical applications, it is an object of the invention to provide genetically engineered endothelial cells which can be used to improve the success of such surgical procedures as coronary angioplasty and vessel graft and stent implantation.

To achieve the foregoing and other objects, the invention provides endothelial cells which have been genetically engineered to produce increased amounts of pp60$^{c-src}$. As shown in the examples presented below, such genetically engineered cells exhibit enhanced cell migration and enhanced u-PA production and thus address the long-standing problems in the field of vascular surgery of endothelial layer reconstruction and thrombus inhibition at the surgical site.

The accompanying figures, which are incorporated in and constitute part of the specification, illustrate certain aspects of the invention, and together with the description, serve to explain the principles of the invention. It is to be understood, of course, that both the figures and the description are explanatory only and are not restrictive of the invention.

DESCRIPTION OF THE PREFERRED EMBODIMENTS

Figure 1:
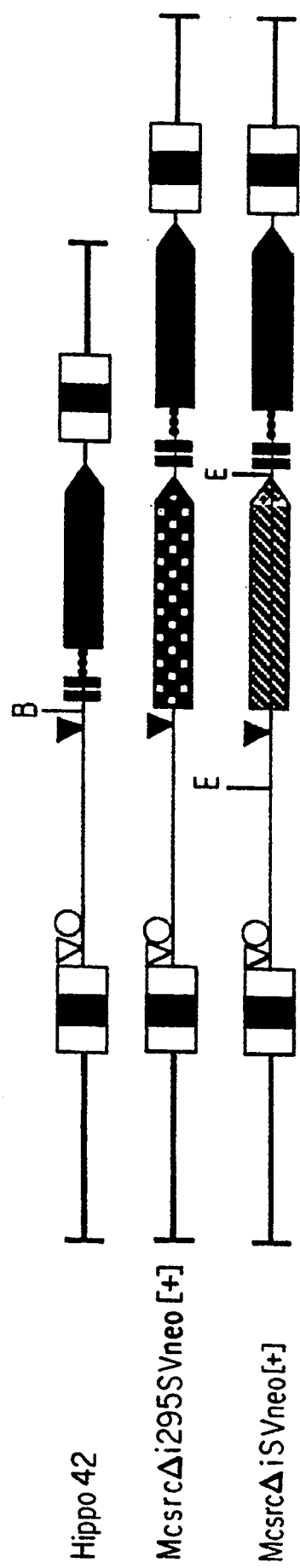
FIG. 1 shows the structure of the three retroviral vectors used in the examples. The abbreviations used in this figure are as follows: rectangular box with a central bar—LTR; open triangle—5' splice site; open circle—ψ packaging signal; closed triangle—3' splice site; solid arrow—Neo$^r$; dotted arrow—Δi295 (kinase-deficient) mutant; stripped arrow—c-src gene; double vertical bar and attached dotted line—SV40 early region promoter-enhancer; solid line—rat genomic DNA; E—EcoRI; B—BamHI.

As discussed above, the present invention relates to endothelial cells which have been genetically engineered to express elevated levels of the pp60$^{c-src}$protein.

The endothelial cells are obtained from the lining of a portion of the vascular system, e.g., a blood vessel or capillary, and are maintained in a tissue culture or other suitable biological medium. The cells will generally be from the patient being treated, although they can be from another individual or another species, e.g., porcine or bovine endothelial cells which can be readily obtained in large quantities, provided that anti-rejection therapies are used to control rejection of the non-autologous cells upon implantation.

Insertion of one or more copies of the coding sequence of the c-src gene i.e., the DNA encoding the c-src polypeptide, into the endothelial cells is accomplished using conventional genetic engineering techniques now known or subsequently developed, i.e., recombinant DNA methodology. For example, retroviral vectors, electroporation, calcium-phosphate techniques, adenovirus vectors, or other means of gene transfer can be used for this purpose. Whatever technique is chosen, a promoter will in general be included with the structural gene so that the pp60$^{c-src}$ protein or a selected portion thereof (see below) will be expressed in the modified endothelial cell.

Various vectors containing the coding sequence of the c-src gene are known in the art. For example, copies of this gene have been previously cloned into the pMc-srcΔiSVneo and p5H plasmids. See Warren et al., supra, and Levy, J. B., H. Iba, and H. Hanafusa. 1986. "Activation of the transforming potential of pp60$^{c-src}$ by a single amino acid change," Proc. Natl. Acad. Sci. USA 83:4228–4232. Deposits of the related v-src gene are available from the American Type Culture Collection, Rockland, Maryland, in the vectors pEcoRIB, Rous sarcoma virus v-src oncogene (v-src), and pPvuIIE, Rous sarcoma virus v-src oncogene (v-src), (ATCC Accession Nos. 41005 and 41006, respectively).

In view of the fact that c-src gene is highly conserved in all species and the fact that the c-src and v-src genes are substantially similar (see Takeya and Hanafusa, supra), these previously cloned c-src genes and/or the deposited v-src genes can be readily used to screen genetic libraries for the c-src gene for any particular species that may be desired. Examples of the types of approaches which can be used appear in the work of Anderson et al., 1985, supra, and Tanaka et al., 1987, supra, which are directed to the human c-src gene and protein. For clinical applications, the human c-src gene, sequenced by these workers, is generally preferred.

The DNA coding and amino acid sequences for representative c-src genes are set forth below in the Sequence Listing. In particular, SEQ. ID. NOS. 1 and 2 set forth the nucleotide and amino acid sequences for the c-src gene and the pp60$^{c-src}$ protein in the chicken, while SEQ. ID. NOS. 3 and 4 set forth the corresponding sequences in the human.

As detailed by Anderson et al., 1985, supra, and Tanaka et al., 1987, supra, these nucleotide and amino acid sequences exhibit very high levels of homology. Thus, the average amino acid sequence homology for these two very diverse species is 98% for exons 3 through 12. Significantly, the kinase active region, as well as the SH2 and SH3 regions which affect protein-protein interactions (see Koch et al., 1991, supra), are contained in these highly conserved portions of the protein molecule. The average homology for exon 2 is 71%, which is still high, although not as high as for exons 3 through 12. As noted by Anderson et al., 1985, supra, exon 1 codes for a 5' untranslated region of mRNA and thus does not appear in the pp60$^{c-src}$ protein.

Similar homologies are seen on the DNA level. Thus, for exons 2–12, the percentage of identical nucleotides in the coding sequences of the chicken c-src gene and the human c-src gene is 85.4% (i.e., 1,374 nucleotides out of a total of 1,608). See Tanaka et al., 1987, supra, Table 1. Moreover, as evidenced by the fact that 94.2% of the amino acids for the chicken and human proteins are identical, Id., the majority of nucleotide changes are silent, third-position codon changes resulting in no amino acid substitutions.

As recognized in the art, the DNA coding and amino acid sequences of the c-src gene/protein for other species are similarly conserved.

In view of these homologies, the terms "c-src gene" and "pp60$^{c-src}$ protein" are used herein to describe these families of substantially similar DNA sequences and resulting proteins, it being understood that any particular member of the family can be used for any particular application either in identical form or with modification provided such modifications do not prevent the gene/protein from exhibiting the effects of enhanced cell migration and/or enhanced u-PA activity. For example, it has been found that the migration and u-PA enhancements described in the examples presented below can also be achieved for a c-src gene which codes for asp, rather than gly, at amino acid position 63 in SEQ. ID. NO. 1.

In this regard, as discussed above, various subregions of the c-src gene/protein are highly conserved, including the SH2 and SH3 domains and the kinase active portion of the protein molecule. These regions, individually or in combination, as well as other subregions of the c-src gene, can be used in the practice of the invention provided they produce the desired effects of enhanced endothelial cell migration and/or u-PA activity.

Depending upon their length, such subregions can be obtained by direct synthesis, by digesting the c-src gene with restriction enzymes, by polymerase chain reaction amplification of all or a part of the desired sequence, or by combinations of such techniques.

The transformation of the endothelial cells is preferably performed in vitro with the transformed cells being implanted directly in the vessel wall using techniques of the type described in Nabel et al., 1989, supra, or used to coat a graft, stent, or similar device which is then implanted. See Wilson et al., 1989, Supra, Dichek et al., 1989, supra, Zeibel et al., 1989, supra, and PCT Patent Publication No. WO 90/06997.

More particularly, endothelial cells, which have been genetically modified to express elevated levels of $pp60^{c\text{-}src}$, can be implanted clinically in a patient's coronary artery by:

1. Harvesting the patient's endothelial cells or selecting endothelial cells which can be implanted in the patient through the use of, for example, anti-rejection techniques or processes.

2. Inserting the c-src gene or a part thereof into the endothelial cells using, for example, a retroviral vector and, in particular, a retroviral packaging system which produces viral vector particles which are free of replicating virus. See, for example, Varmus, H. E. 1982. "Form and Function of Retroviral Proviruses," *Science.* 216:812–820; and Mann, R., R. C. Mulligan, and D. Baltimore. 1983. "Construction of a Retrovirus Packaging Mutant and Its Use to Produce Helper-Free Defective Retrovirus," *Cell.* 33:153–159.

3. Performing diagnostic catheterization of the patient to determine the severity, location and amenability of the coronary (or peripheral) artery disease to angioplasty, atherectomy, laser therapy, or other forms of mechanical revascularization.

4. Assuming step (3) determines that therapeutic angioplasty is appropriate, performing a standard balloon angioplasty procedure.

5. Using a standard wire exchange technique, removing the balloon angioplasty catheter and replacing it with a double balloon catheter having an infusion exit port positioned between the two balloons.

6. Positioning the double balloon catheter tip in the angioplastied coronary artery with the double balloons straddling the denuded segment of the artery, i.e., the portion of the artery in which the endothelial lining has been removed by the angioplasty procedure.

7. Gently inflating the double balloons while supporting the distal coronary circulation with standard perfusion techniques.

8. Introducing the c-src modified endothelial cells into the extracorporeal end of the double balloon catheter and infusing the cells into the isolated space in the blood vessel between the two balloons at a concentration of, for example, $2\text{-}10 \times 10^6$ cells per 10 milliliters of solution to seed the denuded portion of the vessel.

9. After approximately twenty to thirty minutes, deflating the double balloon catheter so as to restore normal antegrade coronary perfusion.

10. Removing the double balloon catheter followed by standard post catheterization procedures.

Similarly, a synthetic or autologous vascular graft or stent can be coated with the c-src modified endothelial cells and then implanted in a patient by:

1. Preparing c-src modified endothelial cells as described in steps (1) and (2) above.

2. Performing diagnostic catheterization of the patient to determine the severity, location and amenability of the coronary (or peripheral) artery disease to vascular bypass surgery with autologous, synthetic, or other graft material.

3. In the case of a synthetic graft or stent, coating the graft or stent with Type I collagen and fibronectin in saturating amounts greater than or equal to 25 $\mu$g/ml in carbonate buffer, pH 9.4; in the case of an autologous graft, harvesting the saphenous vein or other vessel using conventional surgical techniques.

4. Cannulating the proximal end and ligating the distal end of the synthetic or saphenous vein graft.

5. Injecting the c-src modified endothelial cells, at a concentration of, for example, $2\text{-}10 \times 10^6$ cells per 10 milliliters of solution, through the proximal cannulation port into the lumen of the graft and rotating the graft for approximately 60 minutes to allow the c-src modified endothelial cells to cover the graft surface.

6. Implanting the seeded graft in the coronary or peripheral artery using standard fine surgical techniques.

In either case, because the genetically modified endothelial cells express elevated levels of $pp60^{c\text{-}src}$, they exhibit enhanced cell migration thus providing improved and rapid coverage of the denuded vessel or graft in the case of angioplasty or bypass surgery, respectively. Moreover, because the cells also exhibit enhanced u-PA activity, the probability of thrombosis at the vessel wall surface is reduced.

Without intending to limit it in any manner, the present invention will be more fully described by the following examples. The materials and methods which are common to the examples are as follows.

I. Cell culture, migration, proliferation and size

Bovine calf aortic endothelial cells (BAEC) were isolated, cultured with DME (Gibco Laboratories, Grand Island, N.Y.), and characterized as described in Bell, L. and J. A. Madri. 1989. "Effect of platelet factors on migration of cultured bovine aortic endothelial and smooth muscle cells," *Circ. Res.* 65:1057–1065.

Endothelial cells were first seeded into the middle of a steel fence and allowed to attach to the underlying Type I collagen matrix below; after cell attachment, the fence was removed and, with the loss of contact inhibition, the monolayer of cells commenced radial migration outward over a 6 day period.

The role of u-PA in mediating changes in cell migration was evaluated during 3 day migrations of endothelial cells treated with either 5% immune anti-bovine urokinase antiserum administered daily or 5% nonimmune rabbit serum administered daily. See Saksela, O., and D. B. Rifkin. 1990. "Release of basic fibroblast growth factor-heparan sulfate complexes from endothelial cells by plasminogen activator-mediated proteolytic activity," *J. Cell Biol.* 110:767–775.

The possible contribution of changes in cell proliferation during migration was measured by trypsinizing migrating cells and counting aliquots in a Coulter counter (Coulter Electronics, Inc., Hialeah, Fla.).

Cell sizes during migration were measured on approximately 100 cells per treatment by morphometric analysis with a digitizing tablet. See Bell and Madri, 1990, supra.

II. Immunoblot analysis

Cell protein was extracted with RIPA buffer (1% Triton X-100, 1% sodium deoxycholate, 0.1% SDS, 0.15 M NaCl, 0.05 M Tris-HCl, pH 7.2, 1 mM PMSF, and 0.2 mM vanadate) and normalized for total protein using the bicinchonic acid assay. See Smith, P. K., R. I. Krohn, G. T. Hermansion, A. K. Mallia, F. H. Gartner, M. D. Provenzano, E. K. Fujimoto, N. M. Goeke, B. J. Olson and D. C. Klenk. 1985. "Measurement of protein using bicinchonic acid," *Anal. Biochem.* 150:76–85.

Equal protein loads of the cell lysates were run on a 6% reducing polyacrylamide gel, transferred to nitrocellulose paper, blocked with 4% PBSA, and incubated with anti-src monoclonal antibody (MAb327) (Oncogene Science, Inc. Manhasset, NY). See Knecht, D. A. and R. L. Dimond. 1984. "Visualization of antigenic proteins on Western blots," *Anal. Biochem.* 136:180–184; and Blake, M. S., K. H. Johnston, G. J. Russell-Jones and E. C. Gotschlich. 1984. "A rapid, sensitive method for detection of alkaline phosphatase-conjugated anti-antibody on Western blots," *Anal. Biochem.* 136: 175–179. This antibody also immunoblots and precipitates pp60$^{c\text{-}src}$ from cells derived from a wide variety of species including bovine vascular smooth muscle cells and chicken, rat, and canine cells. See DiSalvo, J., D. Gifford, and A. Kokkinakis. 1988. "pp60$^{c\text{-}src}$ kinase activity in bovine coronary extracts is stimulated by ATP," *Biochem. Biophys. Res. Commun.* 153:388–394; Dorai, T., and L. H. Wang. 1990. "An alternative non-tyrosine protein kinase product of the c-src gene in chicken skeletal muscle," *Mol. Cell. Biol.* 10:4068–4079; and Warren et al., 1988, supra. Normal mouse sera was found not to immunoblot or precipitate the appropriate 60-kD moiety from bovine, canine, or rat cells.

The immunoblots were developed with rabbit anti-mouse IgG and $^{125}$I-protein A and then exposed to XAR film (Eastman Kodak Co., Rochester, N.Y.) at $-70°$ C. Quantitative determinations of relative amounts of the src protein were performed using a densitometer (Hoefer Scientific Instruments, San Francisco, Calif.).

III. Kinase assay

Cell protein was extracted with RIPA buffer and normalized for total protein as above. Equal amounts of cell protein were then precleared with normal mouse IgG and incubated overnight with MAb327. The antigen/antibody complexes were precipitated with Protein A sepharose beads, washed with RIPA buffer and subsequently suspended in 20 mM Tris-HCl, pH 7.2, 5 mM MgCl$_2$ with 10 $\mu$Ci $\gamma^{32}$ATP/reaction for 10 minutes at 30° C. See Warren et al., 1988, supra. The reaction was stopped with excess unlabeled ATP. The beads were boiled in solubilization buffer, loaded on a 10% reducing polyacrylamide gel, and the gel was developed with Kodak XAR film at $-70°$ C. Quantitative determinations of relative amounts of the src kinase activity were performed using a Hoefer densitometer.

IV. Plasminogen activator activity assay

Urokinase-like plasminogen activator activity was measured using the chromogenic substrate H-D-norleucyl-hexahydrotyrosyl-lysine-p-nitroanilide diacetate salt (American Diagnostica, Inc., Greenwich, Conn.) at a final concentration of 250 mM and human plasminogen at a final concentration of 25 $\mu$g/ml in 120 mM Tris-HCl pH 8.7 as described in Bell and Madri, 1990, supra. The results of this assay were confirmed by plasminogen zymography, modified from Granelli-Piperino and Reich, with final concentrations of non-fat milk 4%, 0.1 M Tris-HCl pH 7.2, 8 $\mu$m/ml plasminogen, and 1.25% agar. See Granelli-Piperino, A. and E. Reich. 1978. "A study of proteases and protease-inhibitor complexes in biological fluids," *J. Exp. Med.* 148:223–234.

V. Northern blot analysis

Total cellular RNA was extracted with 4M guanidinium HCl, 5 mM sodium citrate pH 7.0, 0.1% $\beta$-mercaptoethanol, and 0.5% Sarkosyl, centrifuged on a cushion of 5.7 M CsCl in 0.1 M EDTA, and re-extracted with a 4:1 mixture of chloroform and 1-butanol and ethanol precipitation. See Maniatis, T., E.F. Fritsch and J. Sambrook. 1982. *Molecular cloning: a laboratory manual.* Cold Spring Harbor Laboratory, Cold Spring Harbor, N.Y. 196. Total cellular RNA, 20 $\mu$m per lane, was electrophoresed through a 1% formaldehyde gel, transferred to Nytran filters and prehybridized with 0.5 M sodium phosphate pH 7.2, 7% SDS, 1% BSA, 1 mM EDTA for 2 hours at 65° C. See Mahmoudi, M. and V.K. Lin. 1989. "Comparison of two different hybridization systems in Northern transfer analysis," *Biotech* 7:331–333. The blot was hybridized overnight at 65° C. with a labeled dCT$^{32}$Pc-src DNA probe, washed twice with 2×SSC and 0.1% SDS for 30 minutes at 65° C. and developed against Kodak XAR film at $-70°$ C. See Warren et al., 1988, supra. Quantitative determinations of relative amounts of the src mRNA were performed using a Hoefer densitometer. All immunoblots, kinase assays, and RNA hybridizations were performed at least two times.

VI. Transfections and infections

The c-src coding sequence (SEQ. ID. NO. 1) was spliced into the helper-free Moloney retroviral vector Mcsrc$\Delta$iSVneo[+]. Id. Mcsrc$\Delta$i295SVneo(+), a similar virus which encodes a kinase negative mutant of c-src, Met-295, and a control virus, Hippo42, that encodes Tn5 aminoglycoside phosphotransferase (Neo$^r$) were also employed. See Jove, R., S. Kornbluth and H. Hanafusa. 1987. "Enzymatically inactive p60c-src mutant with altered ATP-binding site is fully phosphorylated in its carboxy-terminal regulatory region," *Cell.* 50:937–43. $\psi$-2 cells were transfected with plasmid DNA using polybrene/DMSO shock. $\psi$-2 cells were selected in G418 (Sigma Chemical Co.) and the filtered media from resistant cells was used to infect $\psi$-AM cells as described in Cone, R.D. and R.C. Mulligan. 1984. "High-efficiency gene transfer into mammalian cells: generation of helper-free recombinant retrovirus with broad mammalian host range," *Proc. Natl. Acad. Sci.* 81:6349–6353. The resulting amphotropic virus was then used to infect subconfluent BAEC which were selected in G418, 400 $\mu$m/ml, until all uninfected BAEC were killed (10 days).

Infection of the endothelial cells and transfer of the c-src gene was readily accomplished following these techniques. The transformed cells were found to grow stably for at least six months and to maintain their genetically altered properties for at least 2 years when frozen.

VII. Immunofluorescence

Migrating cells were washed four times with PBS, fixed with periodate-lysine-paraformaldehyde fixative, permeabilized with 0.2% Triton X-100, and blocked overnight with PBS with 3% BSA. Cells were incubated with either nonimmune rabbit serum or rabbit anti-bovine u-PA antisera and rhodamine conjugated goat anti-rabbit secondary antibody. Cells were examined on a MRC-600 confocal microscope (Bio-Rad Laboratories, Richmond, Calif.). Cells incubated with nonimmune serum demonstrated no detectable staining.

VIII. Statistical analysis

Changes in migration, proliferation, and u-PA activity were analyzed by analysis of variance and correction was made for multiple comparisons using the method of Bonferroni. Statistical significance was assumed for $P < 0.05$.

EXAMPLE 1

Enhanced Migration of Genetically Engineered Endothelial Cells

This example demonstrates the enhanced migration of endothelial cells which have been genetically engineered to express higher than normal levels of $pp60^{c\text{-}src}$.

Using the amphotropic, helper-free retroviral vector McsrcΔiSVneo(+) described above, the c-src gene was transferred into subconfluent bovine aortic endothelial cells (BAEC). In addition, BAEC were infected with the kinase negative c-src mutant, McsrcΔi295SVneo(+), and with a control virus, Hippo42, that encodes Tn5 aminoglycoside phosphotransferase ($Neo^r$). The structures of the retroviral vectors used for these transformations are shown in FIG. 1.

With regard to their general behavior, the c-src infected endothelial cells did not overgrow monolayers or proliferate in suspension, were contact inhibited, exhibited sheet migration, and retained Factor VIII staining. The proliferation rates (determined by cell counting) of migrating cells that expressed elevated c-src levels, elevated levels of the kinase negative mutant, and $Neo^r$ alone did not differ. The cells that expressed elevated levels of c-src appeared rounder and less flattened than the cells expressing $Neo^r$ alone, but their cytoplasmic areas were similar ($552 \pm 19$ vs. $626 \pm 63$ $\mu m^2$, respectively, P=not significant).

The transformed endothelial cells were tested for expression of $pp60^{c\text{-}src}$, production of c-src mRNA, and c-src kinase activity.

The cells transformed with the c-src gene expressed $pp60^{c\text{-}src}$ at higher levels than control BAEC cells (i.e., cells that had undergone no genetic engineering) as evidenced by the fact that the immunoblot assay showed evidence of $pp60^{c\text{-}src}$ after exposure of the XAR film for less than one day to extracts from transformed cells while extracts from control cells required a seven day exposure before evidence of this protein was seen.

The steady state src protein levels for the endothelial cells that expressed the kinase negative mutant were found to be even higher than those for the cells that expressed elevated levels of the c-src protein (i.e., on the order of 11 fold higher). However, no biologic effects were observed as a result of the expression of the kinase negative mutant src protein.

Consistent with the observed protein levels, the steady state level of the c-src retroviral mRNA transcript was fourfold greater in endothelial cells that expressed the kinase negative mutant than in cells that expressed elevated levels of wild-type c-src.

Figure 2:
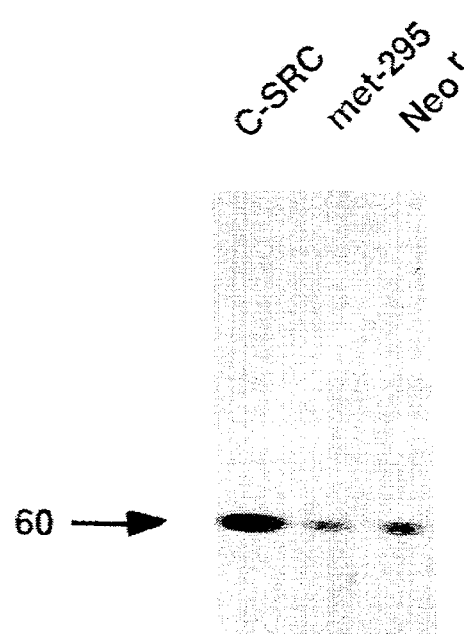
FIG. 2 shows the src kinase activity as determined by the in vitro kinase assay (see below) for cells infected with the vectors of FIG. 1. The following abbreviations are used in this figure and in FIGS. 3, 4, and 6: endothelial cells expressing elevated levels of c-src—C-SRC; endothelial cells cells expressing the kinase negative mutant c-src, met-295—met-295; endothelial cells expressing Tn5 aminoglycoside phosphotransferase alone-—Neo$^r$.

With regard to kinase activity, as shown in FIG. 2, the in vitro src kinase activity was 2–3 fold greater in the cells that expressed elevated levels of c-src than in cells that expressed the kinase negative mutant or $Neo^r$ alone.

Figure 3:
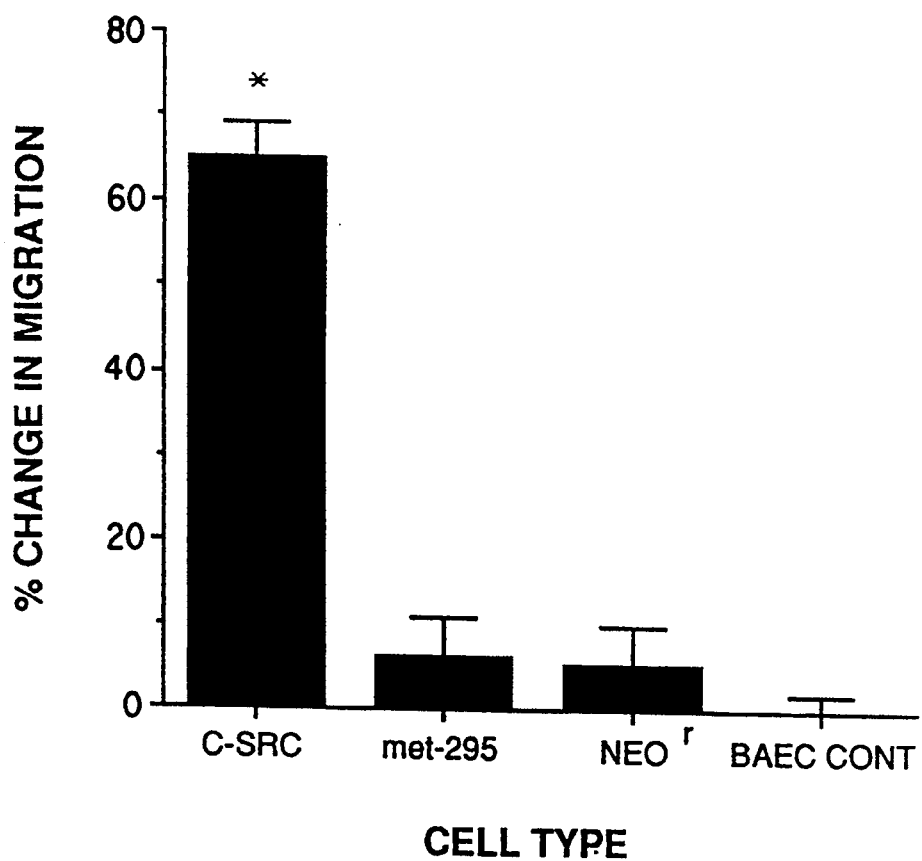
FIG. 3 shows migration rates relative to that of unmodified control cells ("BAEC CONT") of the C-SRC, met-295, and Neo$^r$ cells. The "*" indicates P<0.001 for the C-SRC cells vs. noninfected endothelial cells.

Significantly, with regard to the critical variable of cell migration, it was found that endothelial cells that expressed elevated levels of c-src migrated at a markedly faster rate in the fence assay than cells that expressed the kinase negative mutant, $Neo^r$ alone, or noninfected cells. The results of these experiments are shown in FIG. 3, where each column (bar) represents the result of 8–10 replicates and the mean±1 SEM is shown. The difference between the c-src infected cells and the control cells is statistically significant at the 0.001 level.

As discussed above, the enhanced migration rates shown in FIG. 3 mean that the genetically engineered endothelial cells of the present invention are superior to unmodified cells in terms of their ability to cover denuded sections of blood vessels and/or synthetic or natural grafts.

EXAMPLE 2

Enhanced u-PA Activity of Genetically Engineered Endothelial Cells

This example demonstrates the enhanced u-PA activity of endothelial cells which have been genetically engineered to express higher than normal levels of $pp60^{c\text{-}src}$.

Control and genetically modified cells of the types described above in Example 1 were used for these experiments. u-PA activity was determined as described above.

Figure 4:
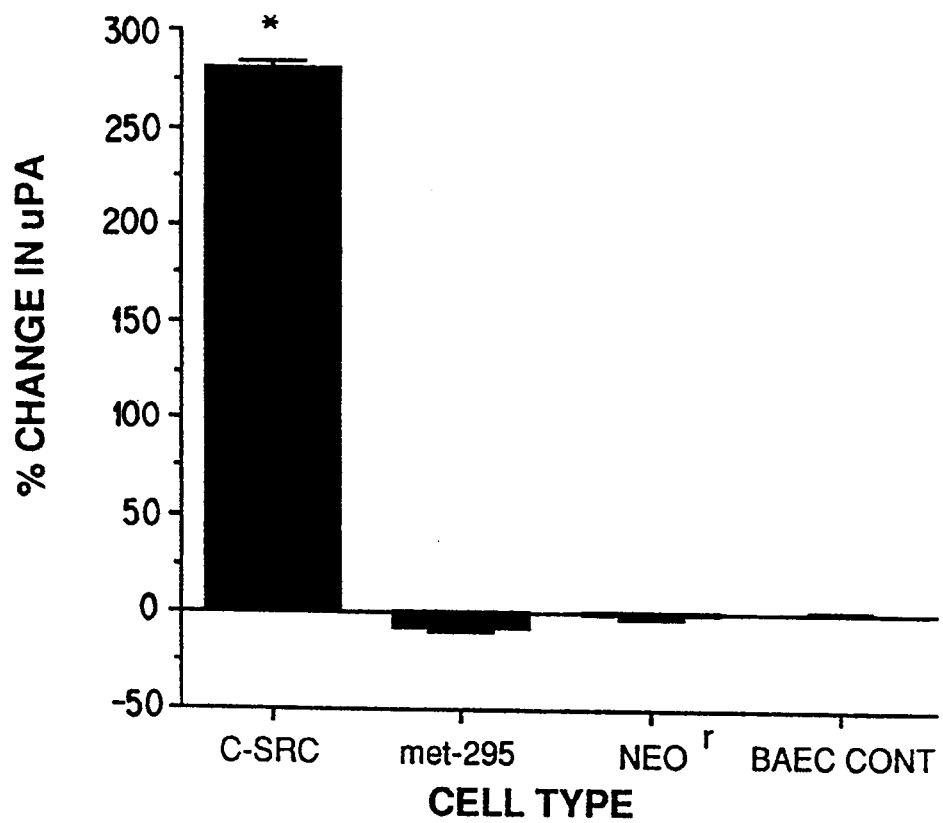
FIG. 4 shows u-PA activity during migration of the C-SRC, met-295, and Neo$^r$ cells relative to that of unmodified control cells. u-PA activity was 4.9±0.05 mPU/μg cell protein in the control cells. The "*" indicates P<0.001 for the C-SRC cells vs. noninfected endothelial cells. Similar results (not shown) were obtained with standard plasminogen zymography.

FIG. 4 shows the results obtained. As shown therein, u-PA activity was significantly greater in endothelial cells that expressed elevated levels of c-src than in cells that expressed the kinase negative mutant, $Neo^r$ alone, or noninfected endothelial cells. Each column (bar) in FIG. 4 represents the result of 5 replicates and the mean±1 SEM is shown. The difference between the c-src infected cells and the control cells was again statistically significant at the 0.001 level.

Figure 5A:
FIGS. 5A and 5B are photomicrographs at the leading edge of migration of Neo$^r$ cells (FIG. 5A) and C-SRC cells (FIG. 5B) which have been stained for u-PA. The bar represents 50 μm.
Figure 5B:
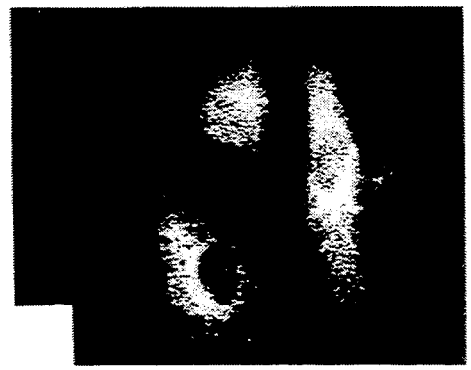

The enhanced production of u-PA is also illustrated by the photomicrographs of FIG. 5. These photographs show the leading edge of the migrating endothelial cells after immunofluorescent staining as described above. FIG. 5A shows cells expressing $Neo^r$ alone, while FIG. 5B shows cells expressing elevated levels of c-src. As can be seen in this figure, the cells which have been genetically modified in accordance with the invention have significantly higher levels of u-PA production. As discussed above, this result means that these cells are superior to unmodified cells in terms of their ability to dissolve and/or prevent thrombus formation at the site of a surgical procedure.

EXAMPLE 3

Interrelationship Between Enhanced u-PA Activity and Enhanced Migration

This example demonstrates that the enhanced migration achieved by the genetically engineered cells of the present invention is at least partially dependent on the enhanced u-PA production of those cells.

Figure 6:
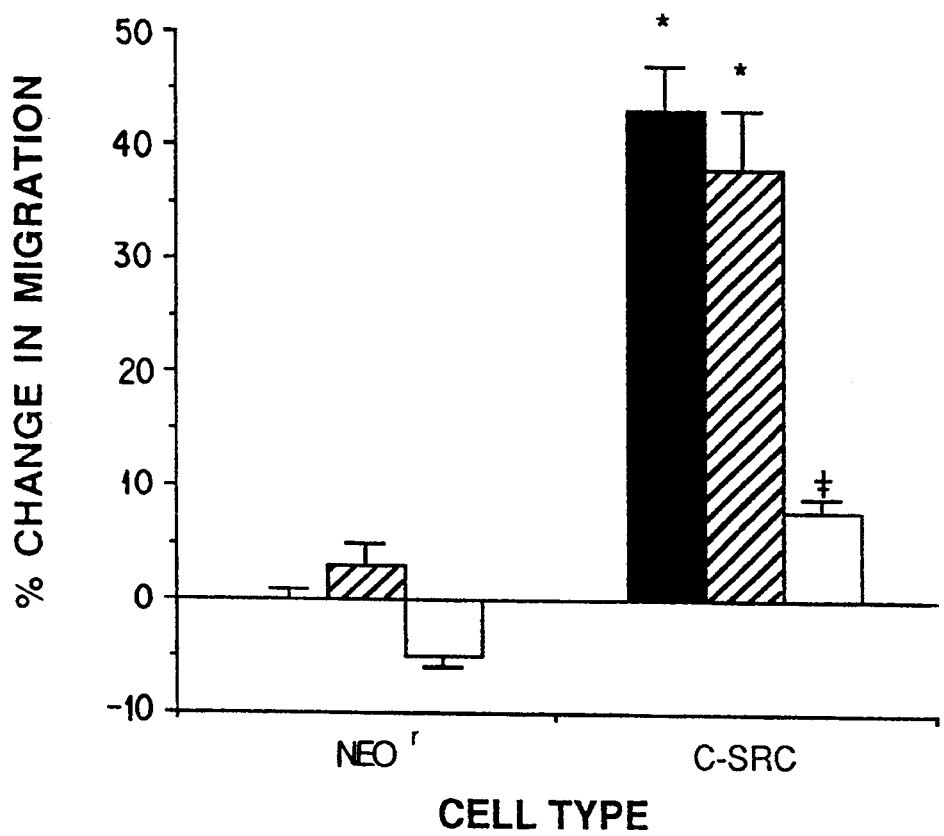
FIG. 6 shows the effect of antisera to bovine u-PA on c-src induced endothelial cell migration. The "*" indicates P<0.001 for the C-SRC cells vs. Neo$^r$cells, and the "‡" indicates P<0.01 for the C-SRC cells incubated with antisera vs. untreated cells.

Antisera to bovine u-PA and nonimmune rabbit antisera were used to demonstrate the dependence. Migrating cells expressing elevated levels of $pp60^{c\text{-}src}$ and $Neo^r$ cells were exposed to the antibodies. The results are shown in FIG. 6, where each column (bar) represents the result of 4 replicates and the mean±1 SEM is shown.

The migration of the two cell types without antisera treatment are shown by the left most (solid) bars. As in Example 2, the c-src cells migrate significantly faster than the Neo$^r$ cells ($P<0.001$). Incubation with nonimmune rabbit antisera did not significantly change the migration of either cell type as shown by the middle (cross-hatched) bars. Incubation with anti-u-PA antisera, however, did significantly reduce the migration of the c-src cells ($P<0.01$) but not that of the Neo$^r$ cells as shown by the right most (open) bars.

As this data shows, there is an interrelationship between the enhanced migration and enhanced u-PA activity exhibited by the genetically engineered cells of the invention in that binding of the u-PA by antibody diminishes the migration rate of the cells.

A variety of modifications which do not depart from the scope and spirit of the invention will be evident to persons of ordinary skill in the art from the disclosure herein. The following claims are intended to cover the specific embodiments described herein as well as such modifications, variations, and equivalents.

What is claimed is:

1. An in vitro culture of endothelial cells, said cells containing a heterologous vector which comprises DNA coding for a c-src polypeptide, wherein the c-src DNA supplied by the heterologous vector effects, upon expression of the c-src polypeptide encoded thereby, enhanced migration or enhanced urokinase plasminogen activator activity or enhanced tyrosine kinase activity compared endothelial to cells which do not contain the heterologous vector, and said endothelial cells containing the heterologous vector retain the nontransformed endothelial cell phenotype.

2. The culture of claim 1 wherein the DNA coding for the c-src polypeptide is operably linked to a promoter.

3. The culture of claim 2 wherein the promoter is a heterologous promoter.

4. The culture of claim 1 wherein the cells are human endothelial cells.

5. An in vitro culture of endothelial cells, said cells containing a heterologous vector which comprises DNA coding for at least a fragment of a c-src polypeptide, wherein said fragment effects enhanced migration of said cells in comparison to endothelial cells which do not contain said heterologous vector, and said endothelial cells containing the heterologous vector retain the nontransformed endothelial cell phenotype.

6. An in vitro culture of endothelial cells, said cells containing a heterologous vector which comprises DNA coding for at least a fragment of a c-src polypeptide, wherein said fragment effects enhanced urokinase plasminogen activator activity by said cells in comparison to endothelial cells which do not contain said heterologous vector, and said endothelial cells containing the heterologous vector retain the nontransformed endothelial cell phenotype.

7. A prosthesis to be implanted in the vascular system of an animal comprising a tubular support carrying endothelial cells from the culture of claim 1.

8. The prosthesis of claim 7 wherein the tubular support comprises an autologous vascular graft.

9. The prosthesis of claim 7 wherein the tubular support comprises a synthetic vascular graft.

10. The prosthesis of claim 7 wherein the tubular support comprises a stent.

11. The prosthesis of claim 7 wherein the endothelial cells containing the heterologous vector exhibit enhanced migration in comparison to endothelial cells which do not contain the heterologous vector.

12. The prosthesis of claim 7 wherein the endothelial cells containing the heterologous vector exhibit enhanced urokinase plasminogen activator activity in comparison to endothelial cells which do not contain the heterologous vector.

13. The prosthesis of claim 7 wherein the endothelial cells containing the heterologous vector exhibit enhanced tyrosine kinase activity in comparison to endothelial cells which do not contain the heterologous vector.

14. The prosthesis of claim 7 wherein the DNA coding for the c-src polypeptide is operably linked to a promoter.

15. The prosthesis of claim 14 wherein the promoter is a heterologous promoter.

16. The prosthesis of claim 7 wherein the endothelial cells are human endothelial cells.

17. A prosthesis to be implanted in the vascular system of an animal comprising a tubular support carrying endothelial cells from the culture of claim 5.

18. A prosthesis to be implanted in the vascular system of an animal comprising a tubular support carrying endothelial cells from the culture of claim 6.

19. The culture of claim 1 wherein the cells containing the heterologous vector exhibit at least a 25 percent enhancement in migration or exhibit at least a 25 percent enhancement in urokinase plasminogen activator activity in comparison to endothelial cells which do not contain the heterologous vector.

* * * * *

UNITED STATES PATENT AND TRADEMARK OFFICE
CERTIFICATE OF CORRECTION

PATENT NO. : 5,336,615
DATED      : August 9, 1994
INVENTOR(S) : Leonard Bell, Joseph A. Madri, Stephen L. Warren, and Daniel J. Luthringer It is certified that error appears in the above-identified patent and that said Letters Patent is hereby corrected as shown below:

Column 5, line 32,  "pp60$^{\text{¢-sr¢}}$" should read "pp60$^{\text{c-src}}$"

Column 7, line 23,  "Neo$^{\text{r}}$cells" should read "Neo$^{\text{r}}$ cells"

Column 31, line 27, "endothelial to cells" should read "to endothelial cells"

Signed and Sealed this

Twentieth Day of December, 1994

Attest:

BRUCE LEHMAN

Attesting Officer      Commissioner of Patents and Trademarks

UNITED STATES PATENT AND TRADEMARK OFFICE
CERTIFICATE OF CORRECTION

PATENT NO. : 5,336,615
DATED : August 8, 1994
INVENTOR(S) : Leonard Bell et al.

It is certified that error appears in the above-identified patent and that said Letters Patent is hereby corrected as shown below:

Column 1, line 13:    insert the following:

The invention identified above is a subject invention under 35 U.S.C. 200, et seq., and the Standard Patent Rights Clause at 37 C.F.R. 401.14 or F.A.R. 52.227-11, which are included among the terms of the above-identified grant/contract award from the Public Health Service/National Institutes of Health.

Signed and Sealed this

Twenty-second Day of June, 1999

Attest:

Q. TODD DICKINSON

*Attesting Officer*    Acting Commissioner of Patents and Trademarks